(12) United States Patent
Tsuneoka et al.

(10) Patent No.: US 10,507,308 B2
(45) Date of Patent: Dec. 17, 2019

(54) CARRYING SUPPORT FOR MEDICAL TUBE, MEDICAL TUBE MANUFACTURING SYSTEM USING SUCH CARRYING SUPPORT, MEDICAL TUBE MANUFACTURING DEVICE USING SUCH CARRYING SUPPORT AND MEDICAL TUBE MANUFACTURING METHOD USING SUCH CARRYING SUPPORT

(71) Applicant: KANEKA CORPORATION, Osaka-shi, Osaka (JP)

(72) Inventors: Katsuyuki Tsuneoka, Settsu (JP); Masayasu Shimaru, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 238 days.

(21) Appl. No.: 15/322,391

(22) PCT Filed: May 7, 2015

(86) PCT No.: PCT/JP2015/063189
§ 371 (c)(1),
(2) Date: Dec. 27, 2016

(87) PCT Pub. No.: WO2016/009705
PCT Pub. Date: Jan. 21, 2016

(65) Prior Publication Data
US 2017/0157371 A1 Jun. 8, 2017

(30) Foreign Application Priority Data
Jul. 16, 2014 (JP) .................................. 2014-146127

(51) Int. Cl.
*A61M 25/10* (2013.01)
*A61M 25/02* (2006.01)
(Continued)

(52) U.S. Cl.
CPC ....... *A61M 25/1027* (2013.01); *A61B 1/0011* (2013.01); *A61B 90/50* (2016.02);
(Continued)

(58) Field of Classification Search
None
See application file for complete search history.

(56) References Cited

U.S. PATENT DOCUMENTS

2006/0182913 A1 8/2006 Bertolino et al.

FOREIGN PATENT DOCUMENTS

| JP | 61-170447 A | 8/1986 |
|---|---|---|
| JP | 11-290341 A | 10/1999 |

(Continued)

OTHER PUBLICATIONS

International Search Report for PCT/JP2015/063189 (PCT/ISA/210) dated Aug. 11, 2015 is attached herewith.
(Continued)

*Primary Examiner* — Monica A Huson
(74) *Attorney, Agent, or Firm* — Birch, Stewart, Kolasch & Birch, LLP

(57) ABSTRACT

The present invention is intended to provide a carrying support that grasps work tubes different in length and type such that the lower ends are at the same height, is easy for the worker to carry by hand and realize automatic carrying, and is further capable of fixing the tube end portions to be processed in many cases at a constant height, thereby to assure the degree of freedom of designing manufacturing devices when the carrying support is also used as a jig for the devices. The carrying support is provided with a first grasping part (11) and a second grasping part (12) that grasp both end sides of work tubes (W) bent in middle parts at an upper position and extending downward.

21 Claims, 17 Drawing Sheets

(51) Int. Cl.
*A61B 90/50* (2016.01)
*A61B 1/00* (2006.01)
*B25B 11/00* (2006.01)
*B25B 5/10* (2006.01)
*B25B 5/16* (2006.01)

(52) U.S. Cl.
CPC ............... *A61M 25/02* (2013.01); *B25B 5/10* (2013.01); *B25B 5/163* (2013.01); *B25B 11/00* (2013.01); *A61M 25/1038* (2013.01); *A61M 2025/028* (2013.01)

(56) References Cited

FOREIGN PATENT DOCUMENTS

| | | |
|---|---|---|
| JP | 2003-47590 A | 2/2003 |
| JP | 2005-534407 A | 11/2005 |
| JP | 4846236 B | 12/2011 |
| JP | 2012-40159 A | 3/2012 |
| JP | 2012-531976 A | 12/2012 |
| WO | WO 2004/012804 A2 | 2/2004 |

OTHER PUBLICATIONS

Written Opinion of the International Searching Authority for PCT/JP2015/063189 (PCT/ISA/237) dated Aug. 11, 2015 is attached herewith.

[Fig. 1]
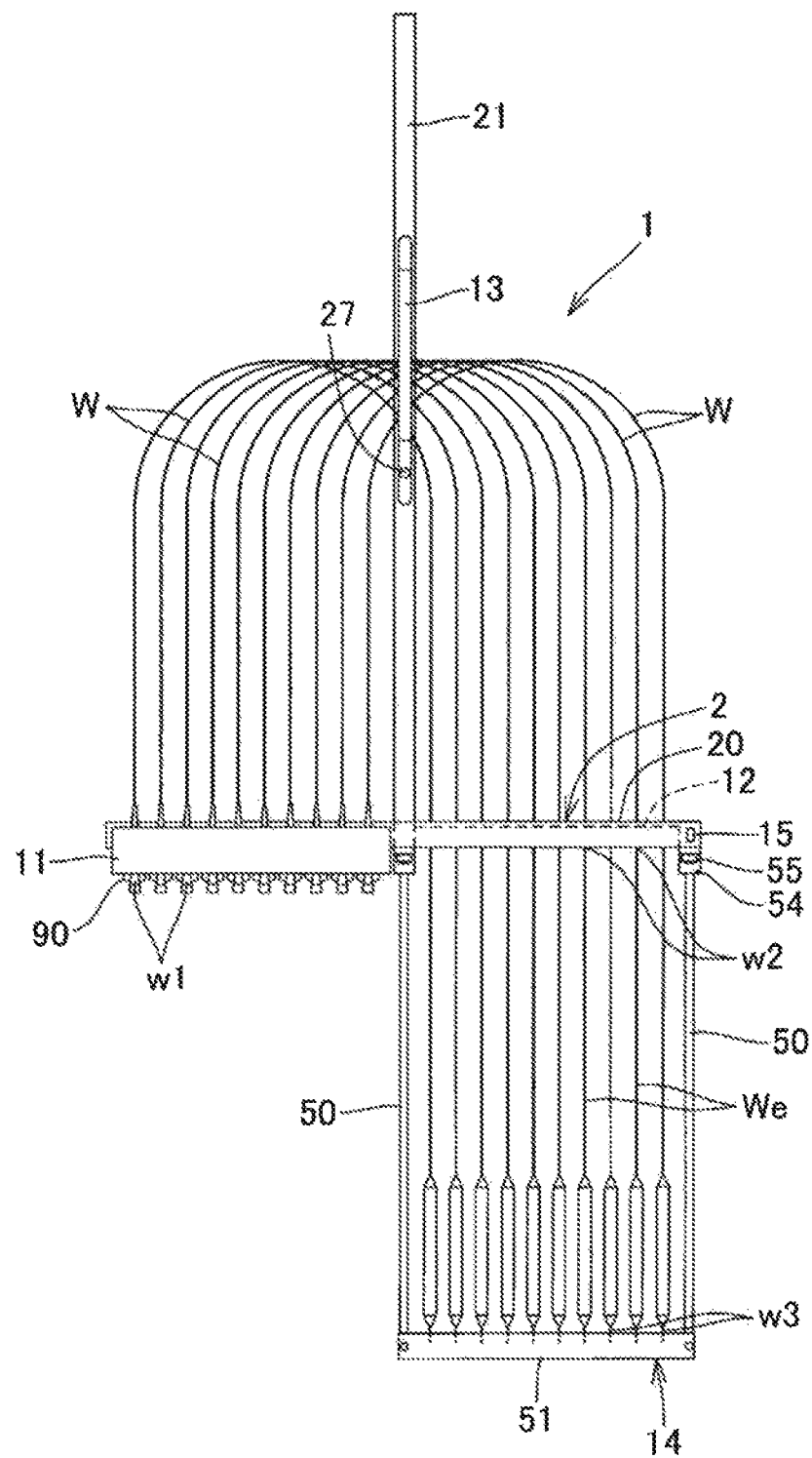

[Fig. 2]
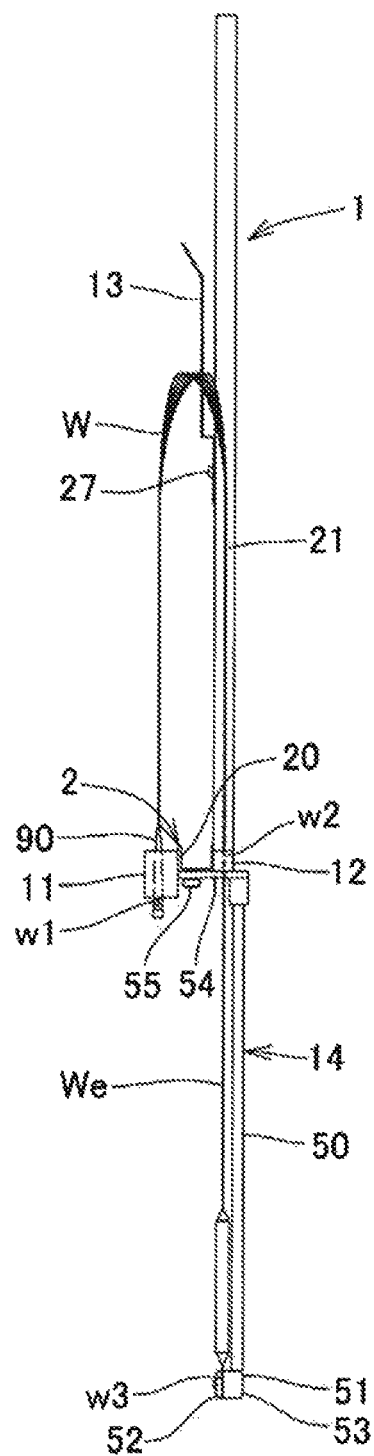

[Fig. 3]
(a)
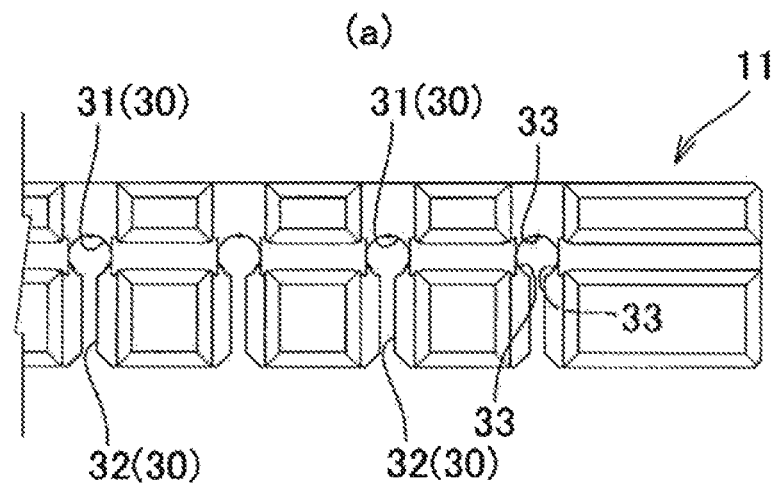
(b)
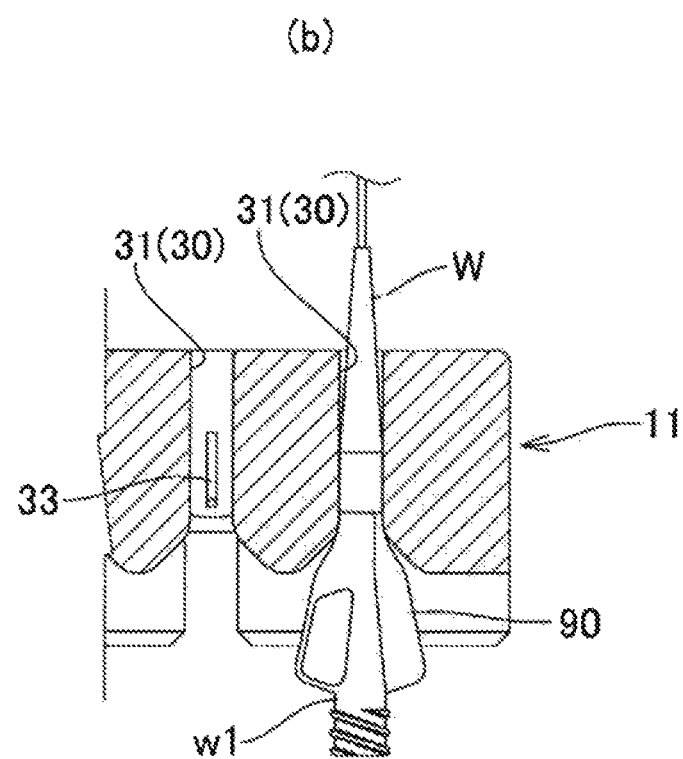

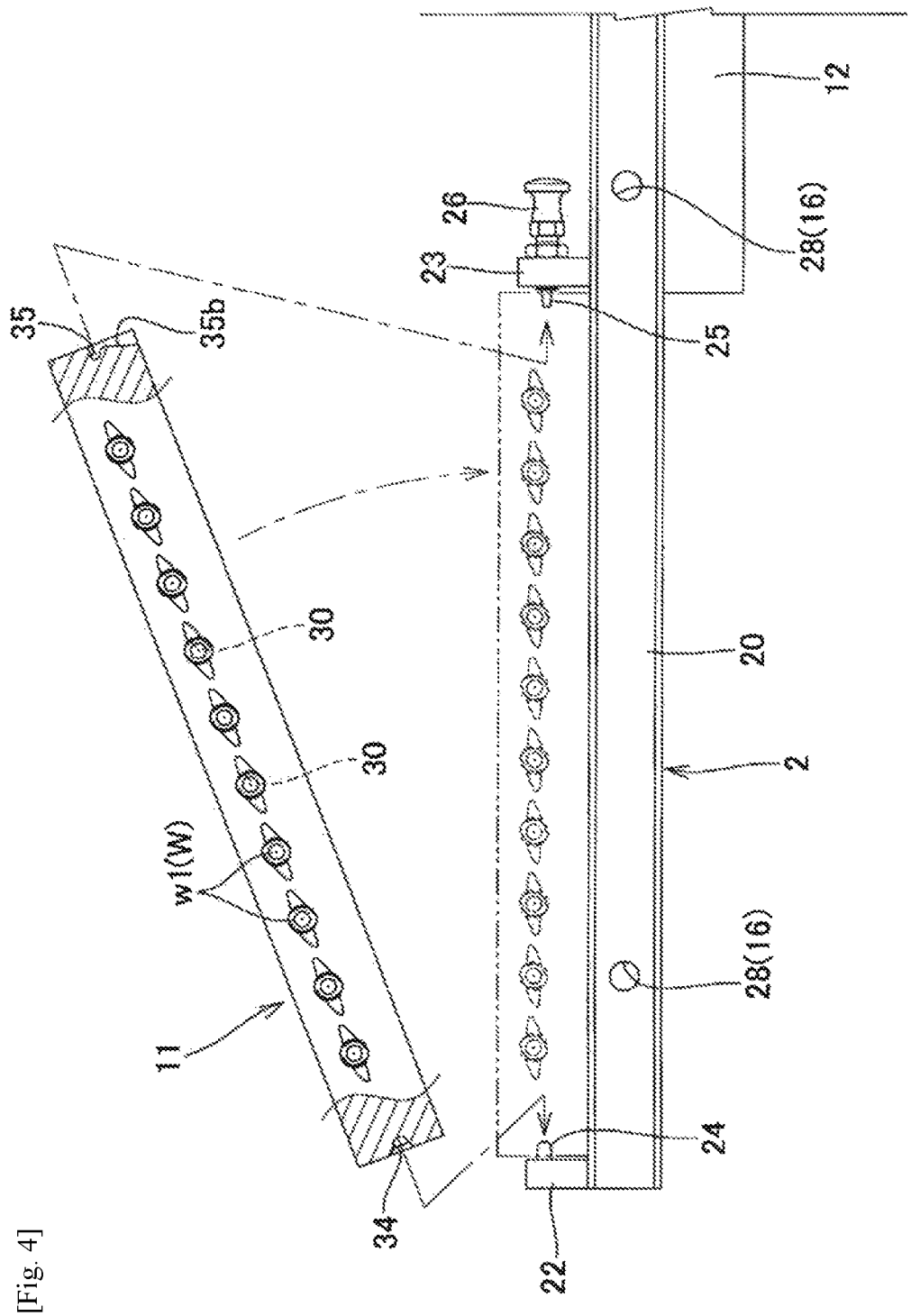
[Fig. 4]

[Fig. 5]
(a)
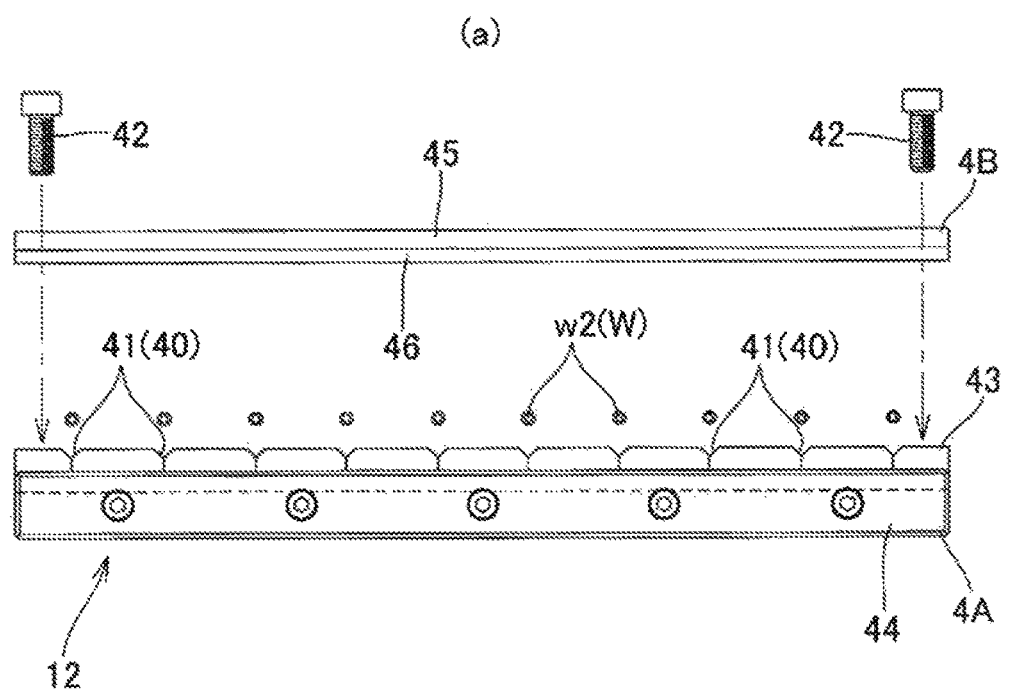
(b)
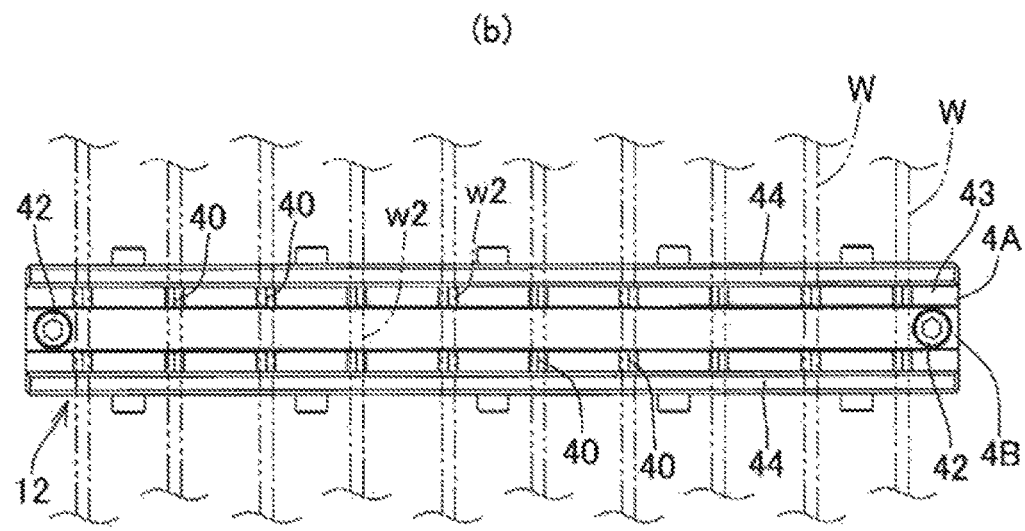

[Fig. 6]
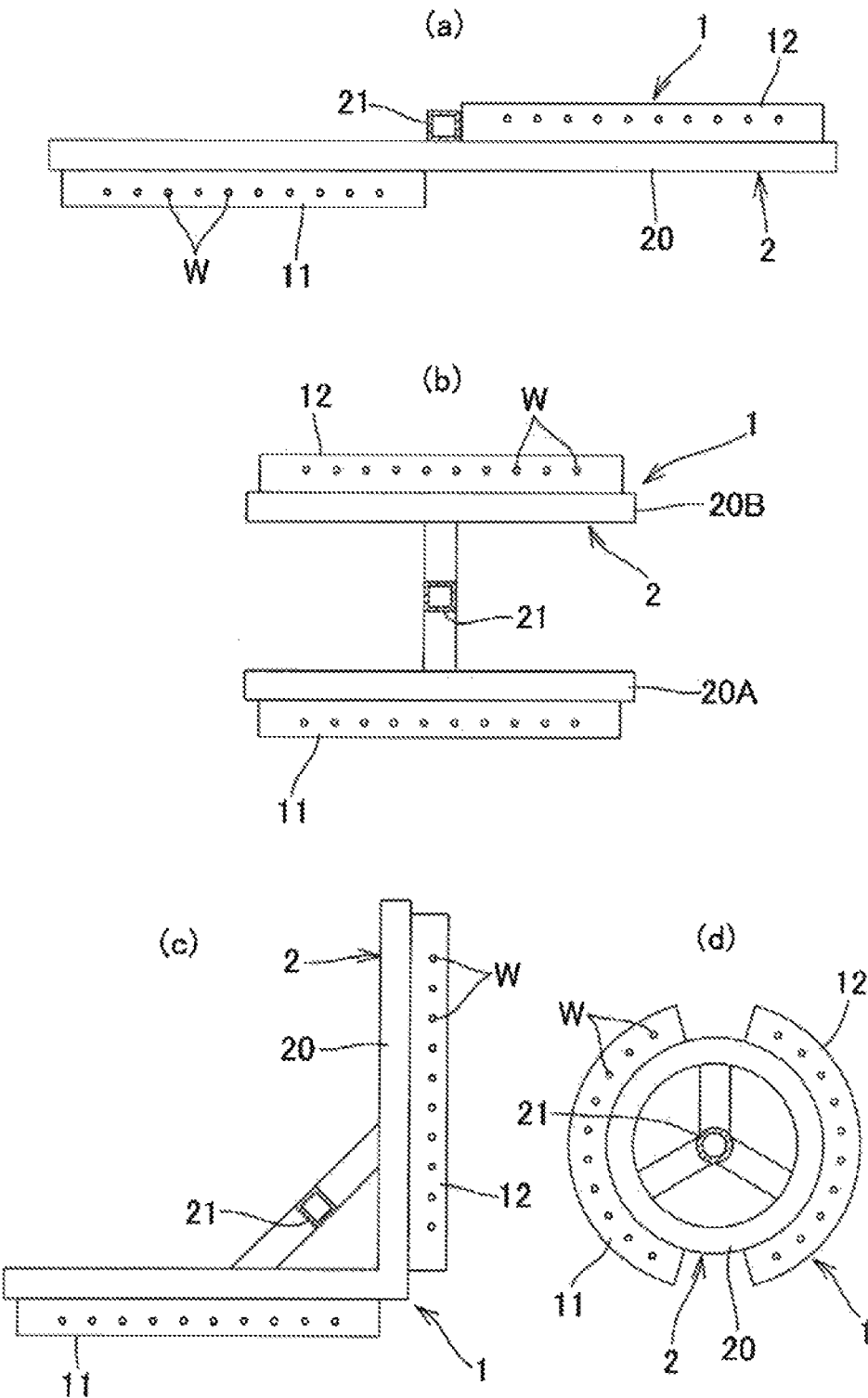

[Fig. 7]
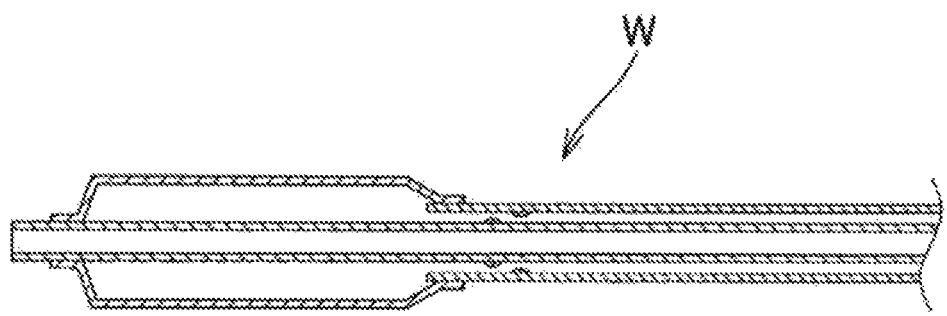

[Fig. 8]
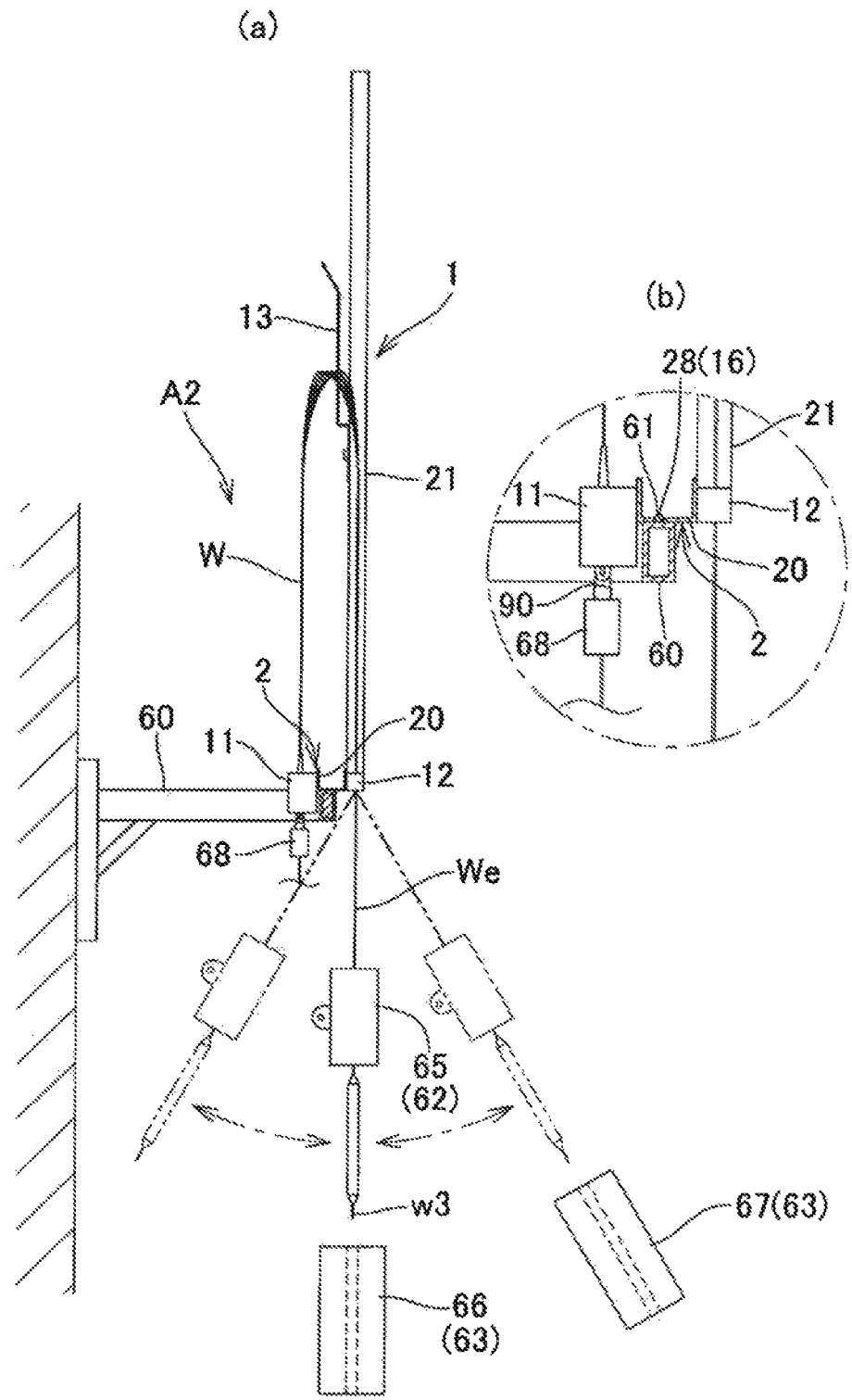

[Fig. 9]
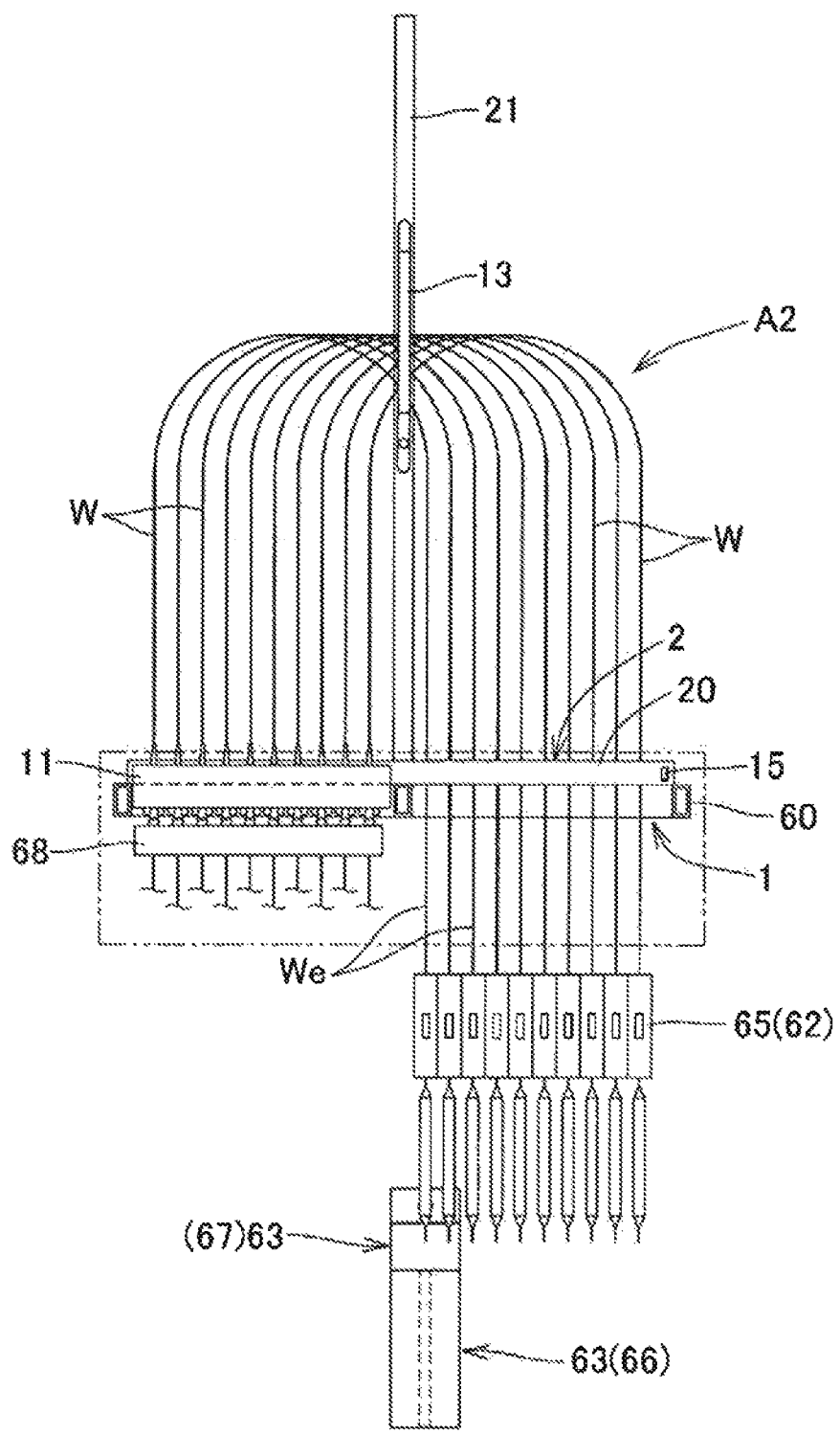

[Fig. 10]
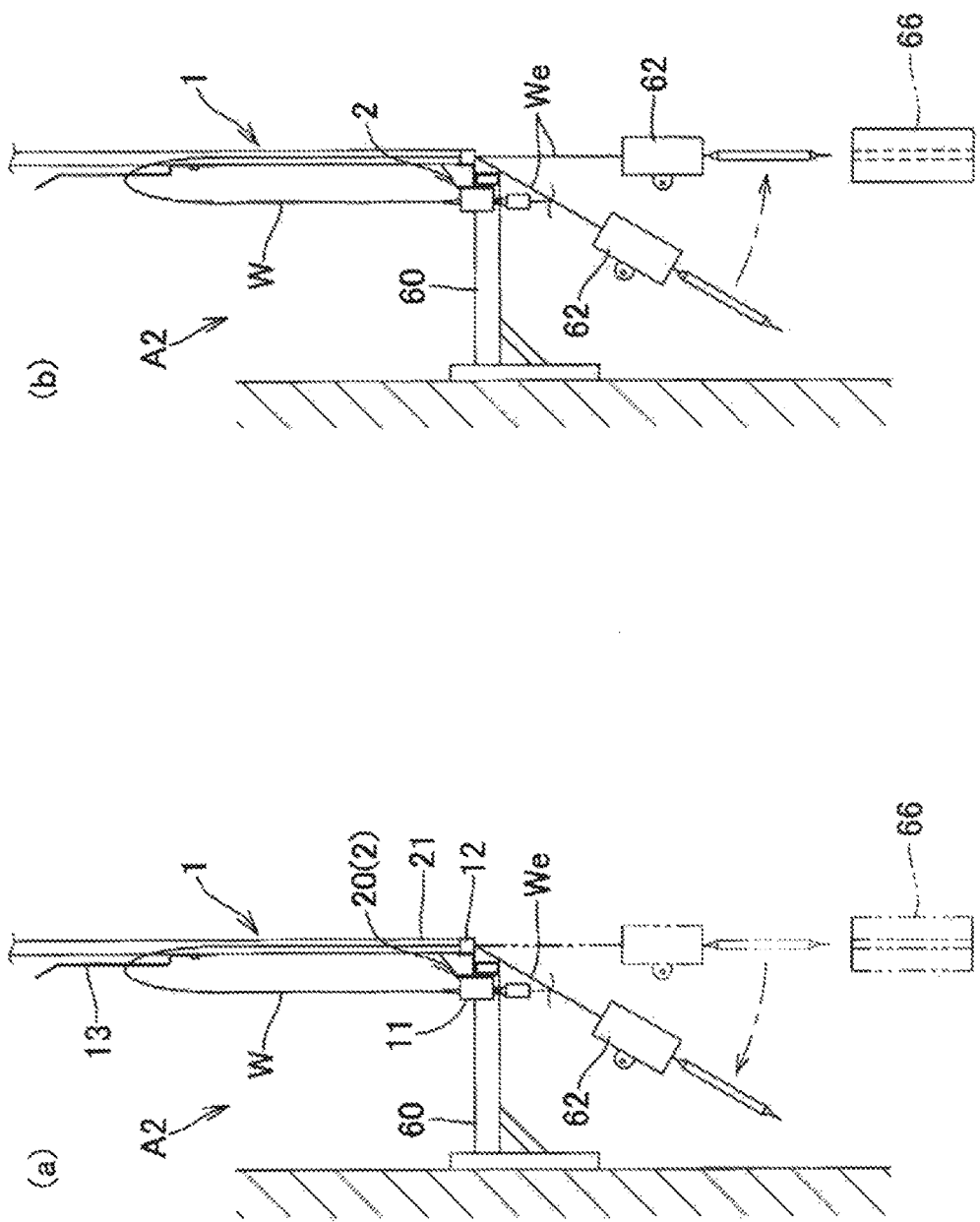

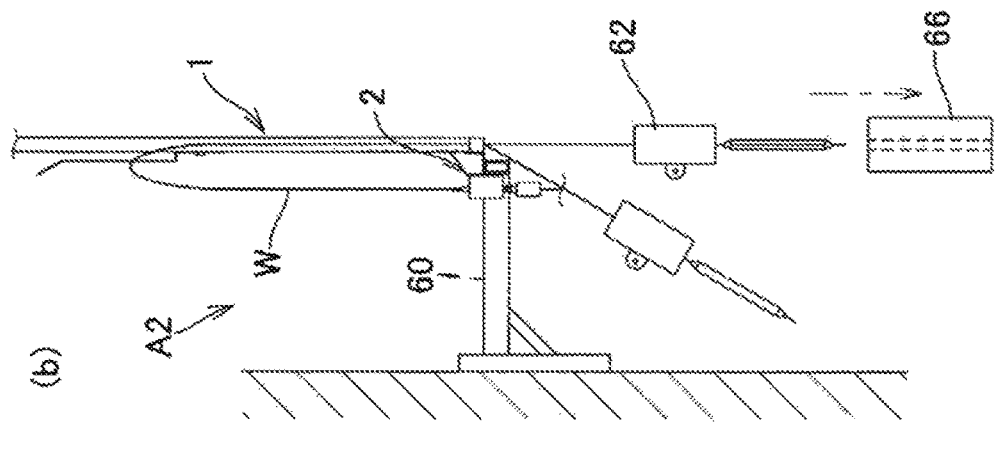
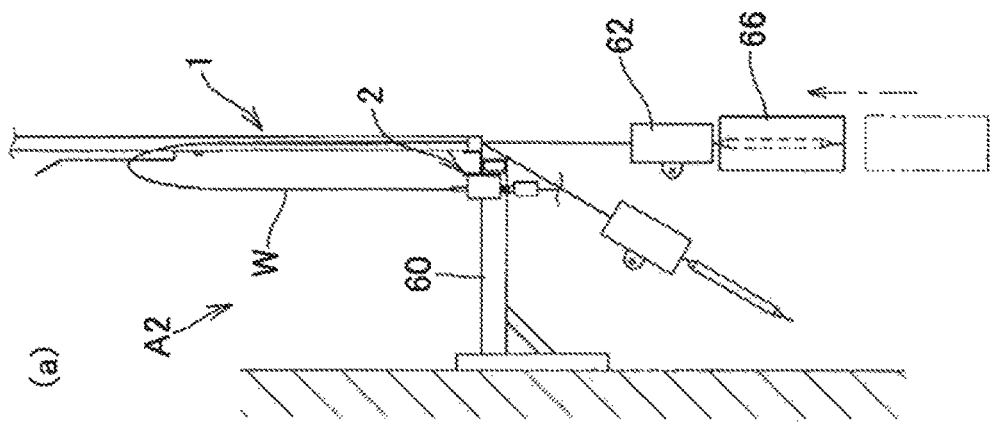
[Fig. 11]

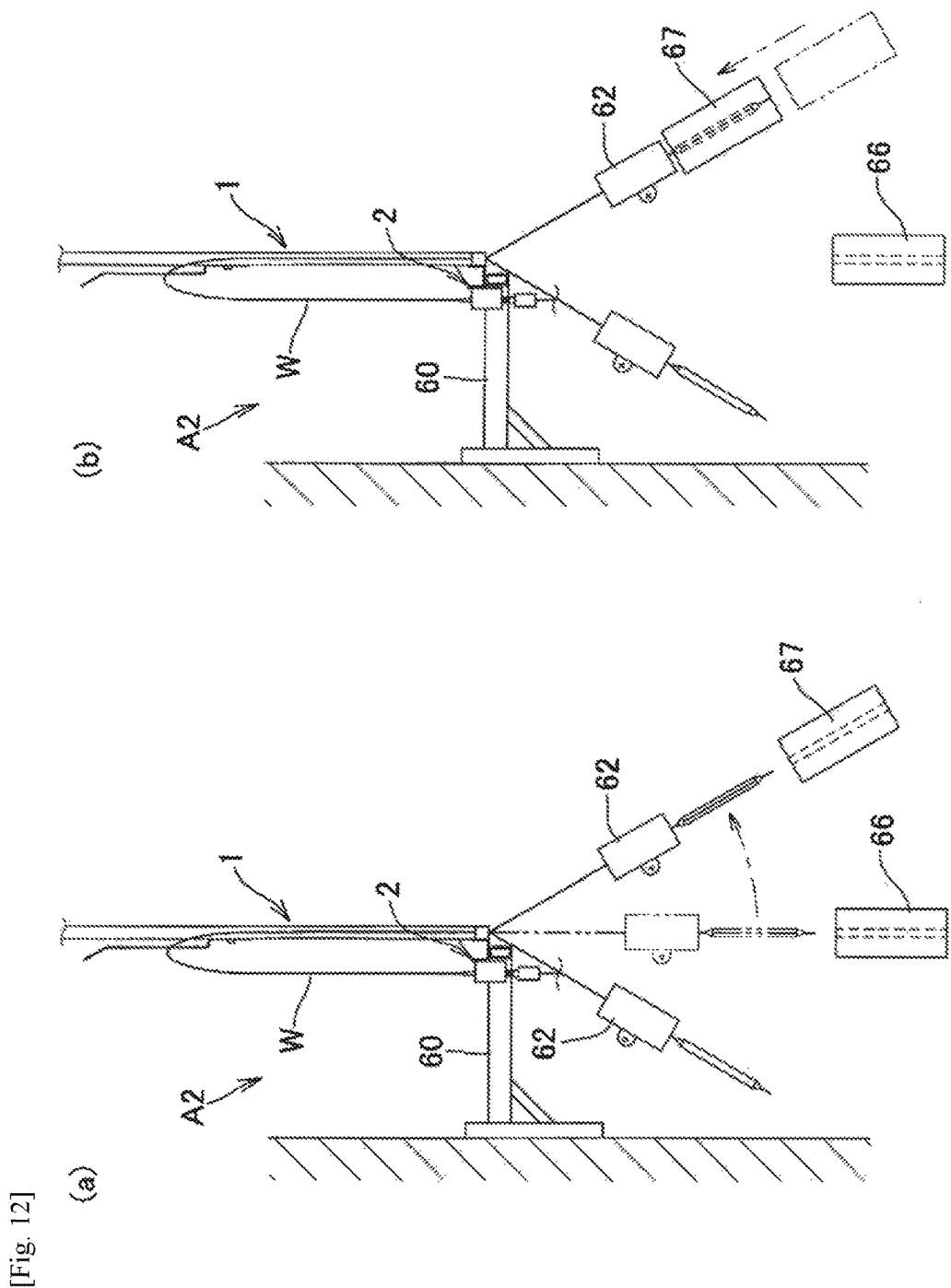

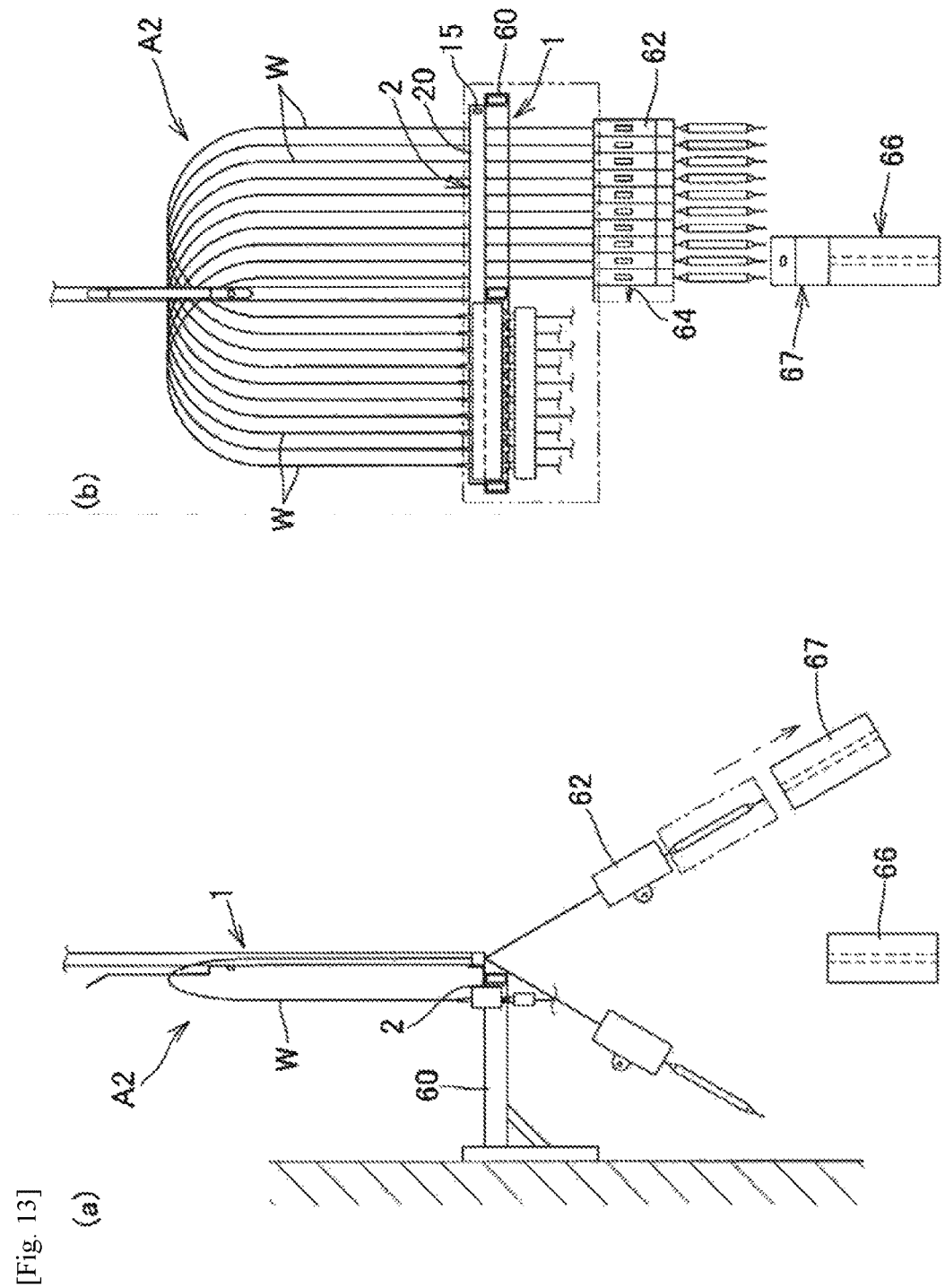

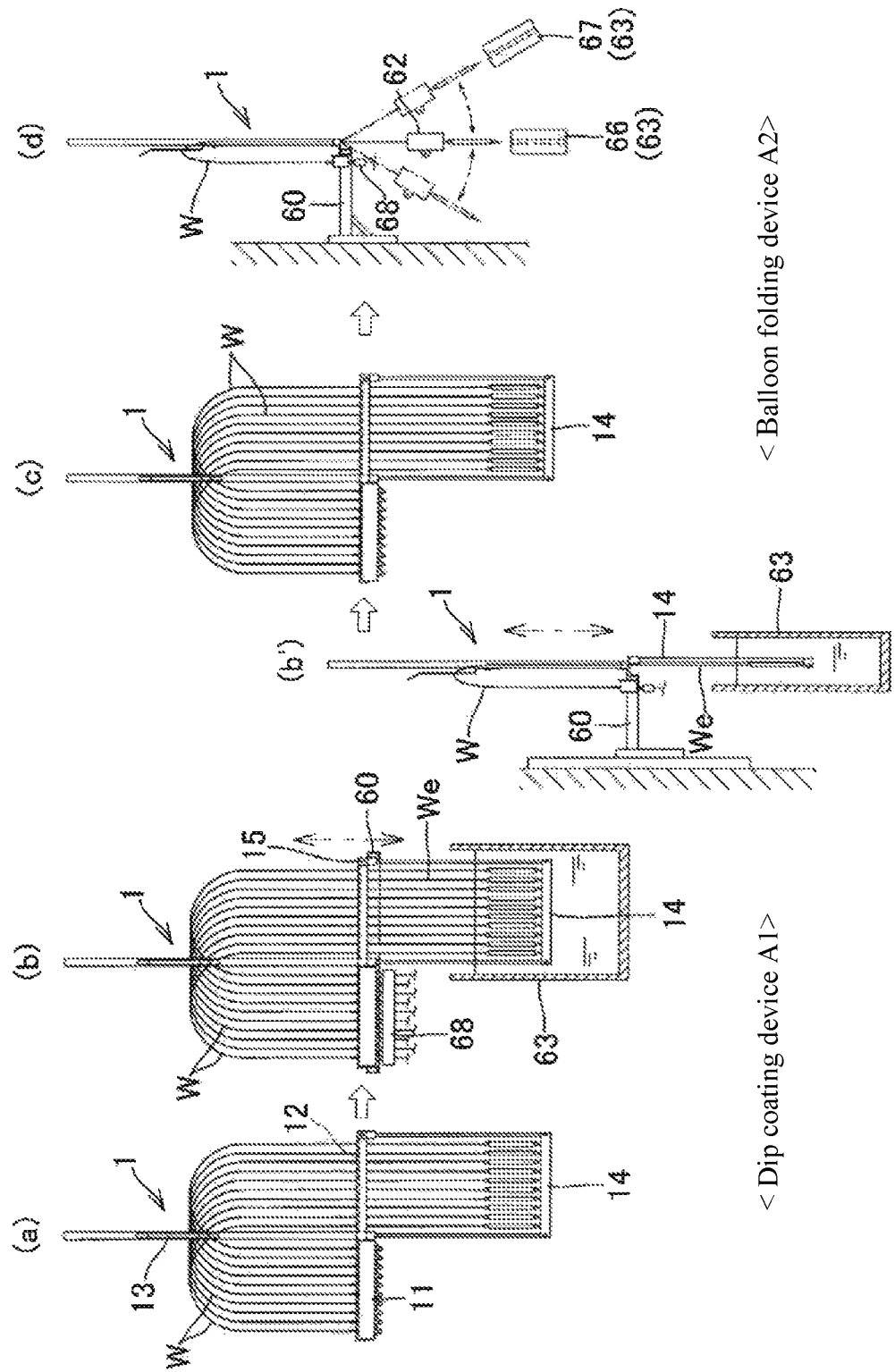

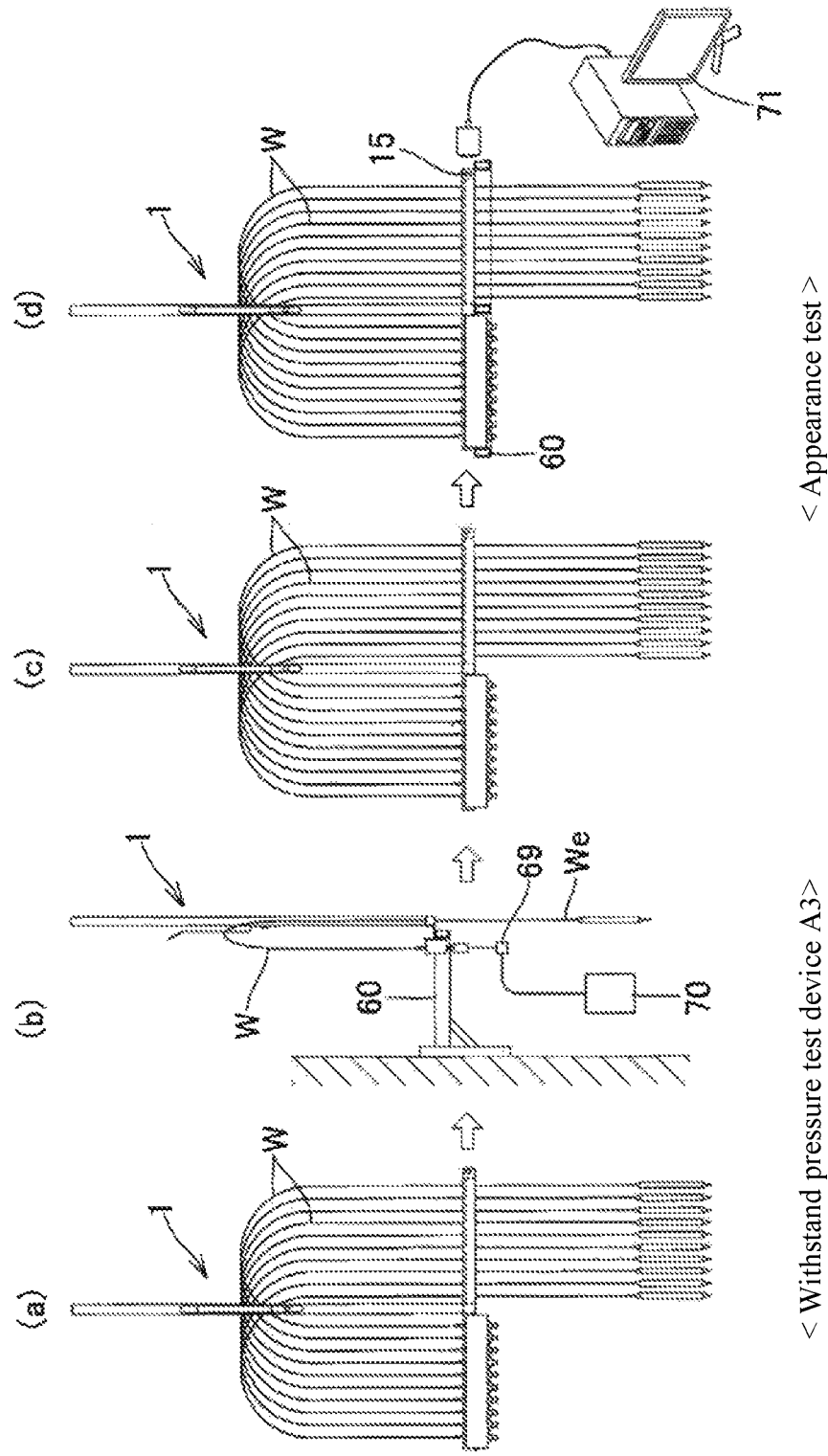
[Fig. 15]

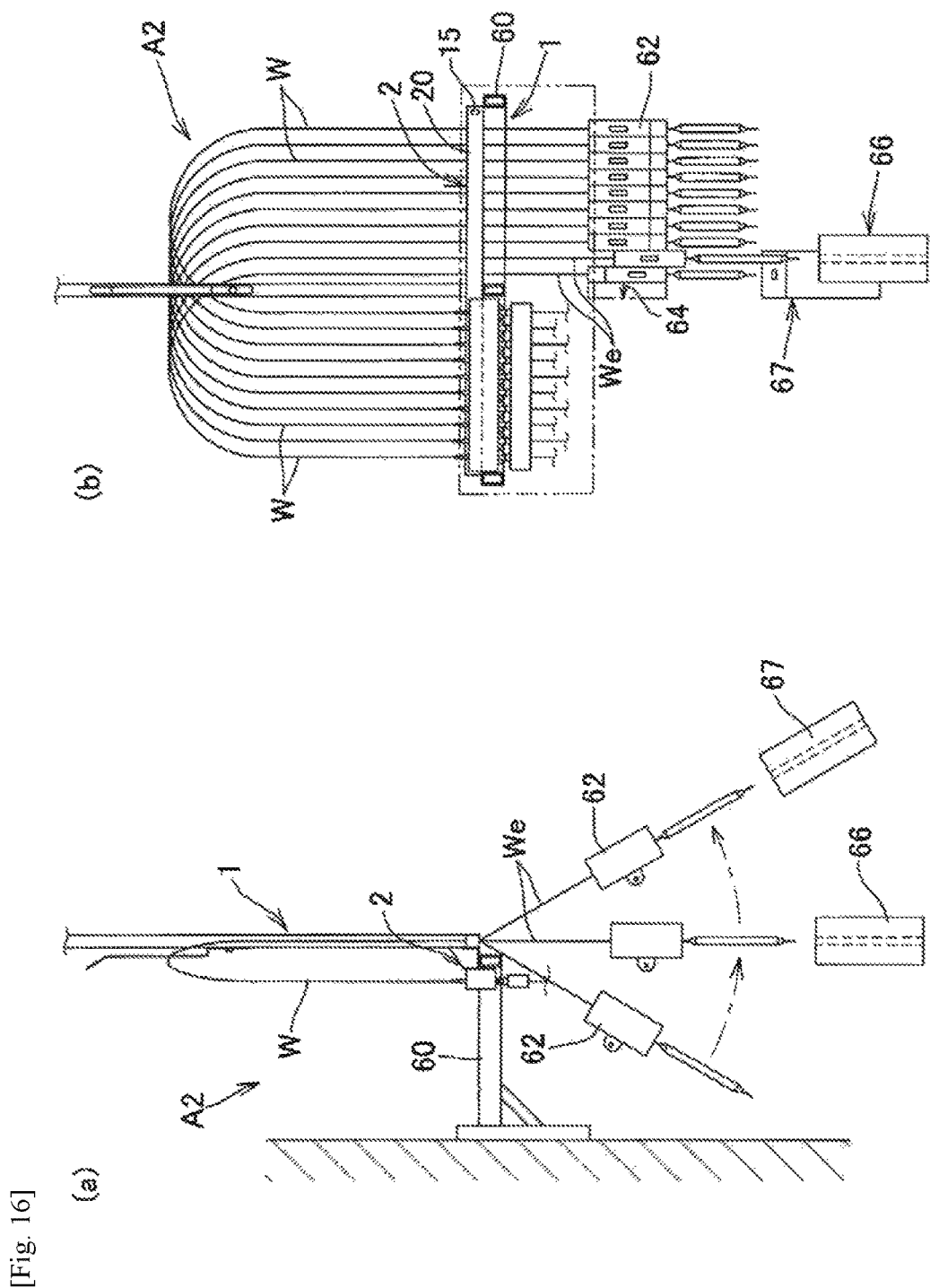

[Fig. 17]
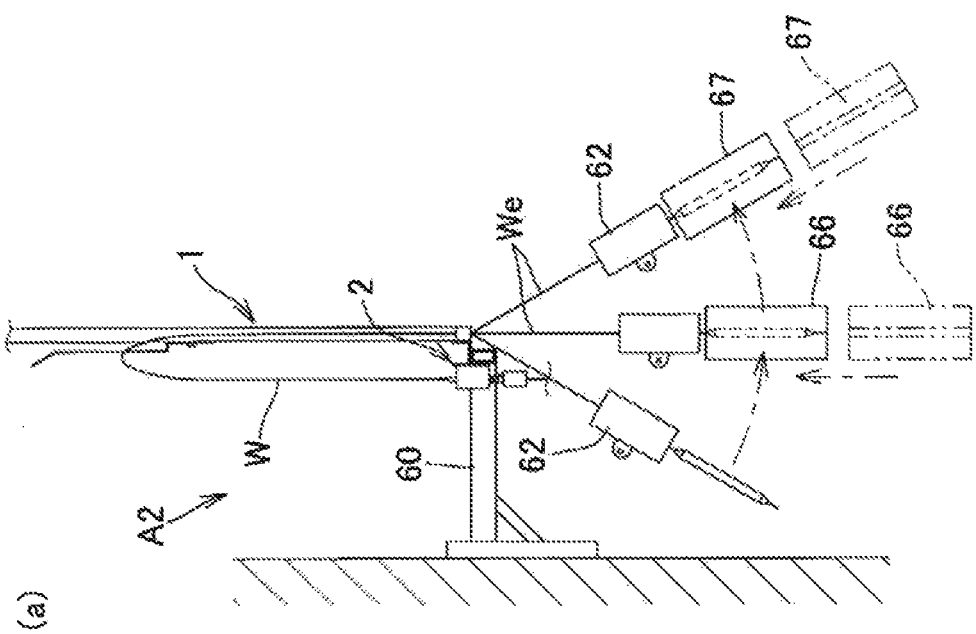
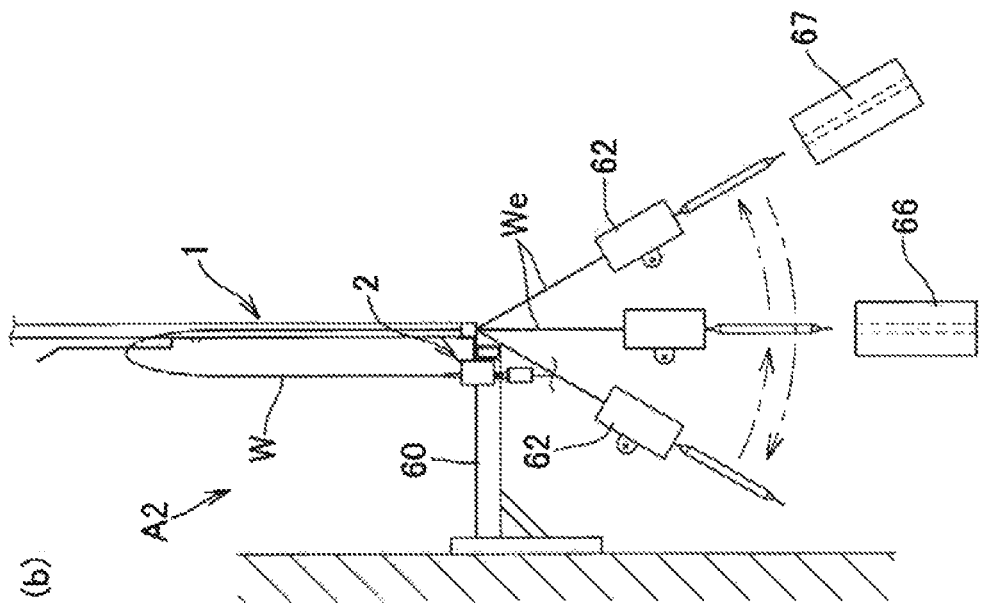

CARRYING SUPPORT FOR MEDICAL TUBE, MEDICAL TUBE MANUFACTURING SYSTEM USING SUCH CARRYING SUPPORT, MEDICAL TUBE MANUFACTURING DEVICE USING SUCH CARRYING SUPPORT AND MEDICAL TUBE MANUFACTURING METHOD USING SUCH CARRYING SUPPORT

TECHNICAL FIELD

The present invention relates to a carrying support for use in the manufacture process of a medical tube, for example, a balloon catheter or the like and relates to a processing device, a manufacturing system, and a manufacturing method using the carrying support.

BACKGROUND ART

In the conventional manufacture of balloon catheters in medical tubes, for example, the catheters are placed sideways in a long "gutter"-like storage container of about 2 m and are carried between the process steps for coating, balloon folding, withstand pressure test, and packaging. At the individual process steps, the catheters are manually taken out and processed one by one, and then returned one by one into the storage container and carried again to the next step.

However, carrying the long storage container takes a lot of work and requires a carrying space for safe carrying to decrease efficiency. In addition, also at the individual process steps, there is need for spaces for placing the long storage container and handling the taken catheters, which results in larger spaces necessary for the individual steps. That is, there are problems of wider spaces required in the manufacturing process and lower area productivity. In addition, manually handling the catheters one by one is required every time at the individual process steps, which requires large number of man-hours and places a certain limitation on improvement of productivity.

Meanwhile, there has been proposed a carrying palette for endoscopic treatment tools that carries flexible, long finite-length sheath coils as endoscopic treatment tools between the working steps in the manufacturing process of the endoscopic treatment tools or supplies the same to devices used in the manufacturing process, wherein the palette includes: a foldable clamp mechanism part that positions and grasps the plurality of sheath coils bent at the both end sides in a vertical U shape and provided in a line and is capable of changing the grasping positions of the sheath coils between a vertical upper direction and a horizontal lateral direction; and a rectangular frame-like main body that supports the foldable clamp mechanism part without interfering with the sheath coils in the vertical U-shaped posture (refer to Patent Document 1).

According to the carrying palette, it is possible to carry a plurality of sheath coils and supply the same to devices used at the process steps with improvement in production efficiency. Since the sheath coils are grasped in the bent state in the vertical U-shaped posture, there is no problem with short sheath coils. However, long sheath coils would largely sag downward, which deteriorates the workability during carrying and makes it difficult to perform automatic carrying. In addition, the both ends of the sheath coils to be processed vary in height from the floor due to the sag, and the sheath coils are hard to handle when being set to the devices at the process steps, thereby causing a problem of placing a burden on designing of the devices.

Patent Document 1: JP-A No. 2003-47590

SUMMARY OF THE INVENTION

Technical Problem

In light of the foregoing circumstances, an object of the present invention is to provide a carrying support that holds work tubes different in length and type such that the lower ends are at the same height, is easy for the worker to carry by hand and realize automatic carrying, and is further capable of fixing the tube end portions to be processed in many cases at a constant height, thereby to assure the degree of freedom of designing manufacturing devices when the carrying support is also used as a jig for the devices.

Solution to Problem

To solve the foregoing problems, the present invention is a carrying support for use in the manufacturing process of medical tubes, including a first grasping part and a second grasping part that grasp both end sides of work tubes bent in middle parts at an upper position and extending downward.

It is preferred that the first grasping part and the second grasping part each have a plurality of grasping portions for each grasping the plurality of work tubes at intervals and are capable of carrying the plurality of work tubes at once.

It is preferred in particular that the first grasping part and the second grasping part are formed such that the plurality of grasping portions for grasping the plurality of work tubes at intervals is arranged in an approximately linear fashion, and the first grasping part and the second grasping part are provided on almost the same plane.

In addition, it is preferred that an upper holding part is provided to hold the middle parts of the bent work tubes at the upper position.

Further, it is preferred that the upper holding part is height-adjustable.

In addition, it is preferred that at least one of the first grasping part and the second grasping part grasps tube outer peripheral surfaces at positions nearer the center by a predetermined length from the end portions of the work tubes.

In addition, it is preferred that the first grasping part grasps end members provided at first ends of the work tubes in a positioned state, and the second grasping part grasps the tube outer peripheral surfaces at positions nearer the center by a predetermined length from second ends of the work tubes.

It is preferred in particular that the tube outer peripheral surfaces are grasped by the first grasping part or the second grasping part, the end portions of the work tubes extending by the predetermined length from the grasping part to the end portions are held at a predetermined position, and an end portion holding member is detachably provided to lay the extending portions of the work tubes between the end portion holding member and the grasping part.

It is also preferred to provide an identification information part capable of being read by a reading device.

It is also preferred to provide an attachment part to be attached to a manufacturing device for use in the manufacturing process.

In addition, the present invention is a medical tube manufacturing system for manufacturing medical tubes by performing processes at a plurality of manufacturing devices with the use of the carrying support according to the present invention, wherein the plurality of manufacturing devices is arranged, each of the manufacturing devices includes: an attachment base to which the carrying support grasping the work tubes by the first grasping part and the second grasping part is attached; and a processing part that processes the extending portions of the work tubes grasped at the tube outer peripheral surfaces at positions nearer the center by the predetermined length from the end portions by the first grasping part or the second grasping part of the carrying support attached to the attachment base and extending from the grasping part to the end portions, and the work tubes grasped by the carrying support are carried to the manufacturing devices, and the work tubes grasped by the carrying support are processed at the manufacturing devices.

In addition, the present invention is a manufacturing device using the carrying support according to the present invention including: an attachment base to which the carrying support grasping the plurality of work tubes by the first grasping part and the second grasping part is attached; a posture change means that, in the plurality of work tubes supported by the carrying support attached to the attachment base and grasped at the tube outer peripheral surfaces at positions nearer the center by a predetermined length from the end portions by the first grasping part or the second grasping part, changes the plurality of extending portions extending from the grasping part to the end portions into a predetermined posture while selectively bending the extending portions; and a processing part that processes the extending portions sequentially changed into different postures by the posture change means.

It is preferred that the manufacturing device includes a position adjustment means that sequentially adjusts relative positions of the extending portions sequentially changed in posture by the posture change means and the processing part such that the relative positional relationship becomes constant.

Specifically, it is preferred that the medical tubes are balloon catheters, the extending portions are leading end-side portions having balloons, and the manufacturing device includes an air supply/absorption means connected to hubs as base end-side end members.

It is preferred in particular that the processing part is a fold processing part for the balloons and is configured as a balloon fold processing device for the balloon catheters.

It is further preferred that the processing part includes, as the fold processing part, a crease application processing part that forms creases in the balloons and a fold application processing part that folds the creases formed by the crease application process in a circumferential direction to form folds.

In addition, the present invention provides a medical tube manufacturing method for manufacturing medical tubes by performing processes at a plurality of manufacturing devices with the use of the carrying support according to the present invention, wherein the plurality of manufacturing devices is arranged, each of the manufacturing devices includes an attachment base to which the carrying support grasping the work tubes by the first grasping part and the second grasping part is attached and a processing part that processes the extending portions of the work tubes grasped at the tube outer peripheral surfaces at positions nearer the center by the predetermined length from the end portions by the first grasping part or the second grasping part of the carrying support attached to the attachment base and extending from the grasping part to the end portions, the work tubes grasped by the carrying support are carried to the manufacturing devices, the carrying support is attached to the attachment bases of the manufacturing devices, and the work tubes grasped by the carrying support are processed by the processing parts of the manufacturing devices.

In addition, the present invention provides a medical tube manufacturing method with the use of the carrying support according to the present invention, wherein the carrying support grasping the plurality of work tubes by the first grasping part and the second grasping part is attached to an attachment base, in the plurality of work tubes supported by the carrying support attached to the attachment base and grasped at the tube outer peripheral surfaces at positions nearer the center by the predetermined length from the end portions by the first grasping part or the second grasping part, the plurality of extending portions extending from the grasping part to the end portions is changed into a predetermined posture while selectively bending the extending portions, and the extending portions sequentially changed into different postures are processed.

It is preferred that relative positions of the extending portions sequentially changed in posture and the processing part performing the process are sequentially adjusted such that the relative positional relationship becomes constant.

It is also preferred that the medical tubes are balloon catheters, the extending portions are leading end-side portions having balloons, and the leading end-side portions having the balloons are processed while air is supplied or absorbed by an air supply/absorption means connected to hubs as base end-side end members.

It is further preferred that the process is a fold process for the balloons, and in particular, the process includes, as the fold process, a crease application process for forming creases in the balloons and a fold application process for folding the creases formed by the crease application process in a circumferential direction to form folds.

Advantageous Effects of Invention

According to the carrying support of the present invention described above, the first grasping part and the second grasping part grasping the both end sides of the work tubes bent in the middle parts at the upper position and extending downward are provided. Accordingly, even when work tubes different in length and type are grasped, the heights of the both end sides can be the same. The worker can easily carry the work tubes by hand because of their uniform height, and automatic carrying can be easily designed and realized. In addition, allowing the both end sides to be fixed at the constant positions, the carrying support can also be easily used as a jig for work tube manufacturing devices for medical tubes where the end portions and their peripheral portions are frequently processed.

In addition, the first grasping part and the second grasping part each have a plurality of grasping portions that grasps a plurality of work tubes at intervals and can carry the plurality of work tubes at once. Accordingly, it is possible to carry the plurality of work tubes efficiently in a stable posture.

In addition, the first grasping part and the second grasping part are each configured such that the plurality of grasping portions is arranged in an approximately linear fashion to grasp the plurality of work tubes at intervals, and the first grasping part and the second grasping part are provided on almost the same plane. Accordingly, the plurality of work tubes can also be collectively grasped on almost the same plane to reduce the area of occupation and improve area productivity.

In addition, when the work tubes are grasped only by the first and second grasping parts, the upper middle parts of the work tubes are shaken during transportation and stress may concentrate on the tubes at the base portions of the grasping parts. However, by providing the upper holding part holding the middle parts of the bent work tubes at the upper position, it is possible to stably hold the middle parts of the work tubes and prevent concentration of stress at the base positions of the grasping parts. In addition, it is possible to prevent unforeseen circumstances such as falling and breakage of the middle parts of the work tubes during carrying.

In addition, providing the height-adjustable upper holding part makes it possible to support work tubes of various lengths.

In addition, at least one of the first grasping part and the second grasping part is a grasping part that grasps the tube outer peripheral surfaces of the work tubes at positions nearer the center by a predetermined length from the end portions of the work tubes. Accordingly, when the work tubes are set on the manufacturing device, the portions of the work tubes extending from the grasping part can be easily positioned as portions to be processed at the processing part.

In addition, the first grasping part is a grasping part that grasps the end members provided at first ends of the work tubes in a positioned state, and the second grasping part is a grasping part that grasps the tube outer peripheral surfaces at the positions nearer the center by a predetermined length from the second ends of the work tubes. Accordingly, it is possible to firmly fix the first ends in the positioned state by the first grasping part, and position at the processing part the second ends extending from the second grasping part as portions to be processed in a stable posture at the individual steps.

The tube outer peripheral surfaces are grasped by the first grasping part or the second grasping part, the end portions of the work tubes extending by the predetermined length from the grasping part to the end portions are held at predetermined positions, and the end portion holding member is detachably provided to lay the extending portions of the work tubes between the end portion holding member and the grasping part. Accordingly, it is possible to carry the work tubes with the extending portions extending from the first or second grasping part held in a stable state, and prevent breakage of the work tubes and the like. In addition, it is possible to efficiently process the extending portions to which the end portion holding member remains attached by coating such as dipping. Even when a plurality of work tubes is provided, it is possible to hold the work tubes in a stable posture without contact with one another at carrying, processing, and drying steps.

In addition, the identification information part readable by a reading device is additionally provided. Accordingly, it is possible to manage information on the attached work tubes such as serial numbers and the like, and easily process and control the work tubes precisely without error according to the types of the work tubes, and manage information on manufacturing failure and the like.

In addition, the attachment part to be attached to the manufacturing devices used in the manufacturing process is provided. By attaching the attachment part to the manufacturing devices, the attachment part can serve as a jig for positioning the work tubes, and the connection to the manufacturing devices can be made uniform to enable efficient production.

In addition, the present invention provides a manufacturing system that manufactures medical tubes by performing processes at a plurality of manufacturing devices with the use of the carrying support according to the present invention, wherein the plurality of manufacturing devices is arranged, each of the manufacturing devices is provided with an attachment base to which the carrying support grasping work tubes by the first grasping part and the second grasping part is attached and a processing part that processes extending portions of the work tubes grasped at tube outer peripheral surfaces at positions nearer the center by a predetermined length from end portions by the first grasping part or the second grasping part of the carrying support attached to the attachment base and extending from the grasping part to the end portions, the work tubes grasped by the carrying support are carried to the manufacturing devices, and the work tubes grasped by the carrying support are processed at the manufacturing devices. Accordingly, the carrying support can be used not only for carrying between the manufacturing devices but also as a jig at the manufacturing devices. This establishes a system in which the work tubes can be efficiently produced while remaining grasped by the carrying support without having to remove the work tubes one by one at the manufacturing devices.

In addition, the present invention is a manufacturing device using the carrying support of the present invention, including: an attachment base to which the carrying support grasping a plurality of work tubes by the first grasping part and the second grasping part is attached; a posture change means that, in a plurality of work tubes supported by the carrying support attached to the attachment base and grasped at tube outer peripheral surfaces at positions nearer the center by a predetermined length from the end portions by the first grasping part or the second grasping part, changes a plurality of extending portions extending from the grasping part to end portions into a predetermined posture while selectively bending the extending portions; and a processing part that processes the extending portions sequentially changed into different postures by the posture change means. Accordingly, it is possible to selectively extract the extending portions by the posture change means and process them one by one at the processing part while the plurality of work tubes is grasped by the carrying support. In addition, the processing part processing the downwardly extending portions is vertically oriented, which makes it possible to reduce the area occupied by the manufacturing device and enhance area productivity.

In addition, the position adjustment means is provided to adjust relative positions of the extending portions sequentially changed in posture by the posture change means and the processing part such that the relative positional relationship becomes constant. Accordingly, it is possible to extract and efficiently process the extending portions in sequence.

In addition, the medical tubes are balloon catheters, the extending portions are leading end-side portions having balloons, and the air supply/absorption means is connected to the hubs as base end-side end members. Accordingly, it is possible to efficiently manufacture various balloon catheters while supplying and absorbing the air.

In addition, the processing part is the fold processing part for balloons and is configured as the balloon fold processing device for balloon catheters. Accordingly, it is possible to efficiently form folds in the balloons of the work tubes while the plurality of work tubes is grasped by the carrying support.

In addition, the processing part includes, as the fold processing part, the crease application processing part that forms creases in balloons and the fold application processing part that folds the creases formed by the crease application process in a circumferential direction to form folds. Accordingly, it is possible to perform the fold processing in a reliable and efficient manner.

In addition, the present invention provides the medical tube manufacturing method by performing processes at the plurality of manufacturing devices with the use of the carrying support according to the present invention, wherein the method includes: arranging the plurality of manufacturing devices, providing each of the manufacturing devices with the attachment base to which the carrying support grasping work tubes by the first grasping part and the second grasping part is attached and the processing part that processes the extending portions of the work tubes grasped at tube outer peripheral surfaces at positions nearer the center by a predetermined length from the end portions by the first grasping part or the second grasping part of the carrying support attached to the attachment base and extending from the grasping part to the end portions; carrying the work tubes grasped by the carrying support to the manufacturing devices; attaching the carrying support to the attachment base of each of the manufacturing devices; and processing the work tubes grasped by the carrying support by the processing parts of the manufacturing devices. Accordingly, the carrying support can be used not only for carrying between the manufacturing devices but also as a jig at the manufacturing devices. This makes it possible to efficiently produce the work tubes while remaining grasped by the carrying support without having to remove the work tubes one by one at the manufacturing devices.

In addition, the present invention provides a medical tube manufacturing method with the use of the carrying support according to the present invention, wherein the method includes: attaching the carrying support grasping a plurality of work tubes by the first grasping part and the second grasping part to the attachment base; in the plurality of work tubes supported by the carrying support attached to the attachment base and grasped at tube outer peripheral surfaces at positions nearer the center by a predetermined length from end portions by the first grasping part or the second grasping part, changing a plurality of extending portions extending from the grasping part to the end portions into a predetermined posture while selectively bending the extending portions; and processing the extending portions sequentially changed into different postures. Accordingly, it is possible to selectively extract the extending portions and process them one by one while the plurality of work tubes is grasped by the carrying support. In addition, the processing part processing the downwardly extending portions is vertically oriented, which makes it possible to reduce the area occupied by the manufacturing device and enhance area productivity.

In addition, relative positions of the extending portions sequentially changed in posture and the processing part performing the process are adjusted such that the relative positional relationship becomes constant. Accordingly, it is possible to extract and efficiently process the extending portions in sequence.

In addition, the medical tubes are balloon catheters, the extending portions are leading end-side portions having balloons, and the leading end-side portions having the balloons are processed while supplying and absorbing the air by the air supply/absorption means connected to the hubs as the base end-side end members. Accordingly, it is possible to efficiently manufacture the medical tubes.

The process is a process for forming folds in the balloons. Accordingly, it is possible to efficiently form folds in the balloons of the work tubes while the plurality of work tubes is grasped by the carrying support.

The process includes as the fold process the crease application process for forming creases in the balloons and the fold application process for folding the creases formed by the crease application process in a circumferential direction to form folds. Accordingly, it is possible to form folds in a reliable and efficient manner.

BRIEF DESCRIPTION OF THE DRAWINGS

FIG. 1 is an explanatory diagram illustrating the used state of a carrying support according to a representative embodiment of the present invention;

FIG. 2 is a side view of FIG. 1;

FIG. 3(*a*) is an explanatory diagram of main components of a first grasping part of the carrying support and FIG. 3(*b*) is a cross-sectional view illustrating the state in which the first grasping part sandwiches an end member;

FIG. 4 is an explanatory diagram illustrating the state in which the first grasping part is attached to a support main body;

FIG. 5(*a*) is a planar view of a second grasping part and FIG. 5(*b*) is a front view of the same;

FIGS. 6(*a*) to 6(*d*) are explanatory diagrams illustrating modification examples regarding placement of the first grasping part and the second grasping part;

FIG. 7 is a cross-sectional view of a work tube of a balloon catheter;

FIGS. 8(*a*) and 8(*b*) are explanatory diagrams illustrating a manufacturing device according to a representative embodiment of the present invention;

FIG. 9 is a front view of the manufacturing device;

FIGS. 10(*a*) and 10(*b*) are explanatory diagrams illustrating a procedure for manufacture by the manufacturing device;

FIGS. 11(*a*) and 11(*b*) are explanatory diagrams illustrating the procedure for manufacture;

FIGS. 12(*a*) and 12(*b*) are explanatory diagrams illustrating the procedure for manufacture;

FIGS. 13(*a*) and 13(*b*) are explanatory diagrams illustrating the procedure for manufacture;

FIGS. 14(*a*) to 14(*d*) are explanatory diagrams illustrating a manufacturing system according to a representative embodiment of the present invention;

FIGS. 15(*a*) to 15(*d*) are explanatory diagrams illustrating the manufacturing system;

FIGS. 16(*a*) and 16(*b*) are explanatory diagrams illustrating a modification example of procedure for manufacture by the manufacturing device according to the representative embodiment; and FIGS. 17(*a*) and 17(*b*) are explanatory diagrams illustrating a modification example of procedure for manufacture.

REFERENCE SIGNS LIST

A1 to A3 Manufacturing device
W Work tube
w1 and w3 End portion
w2 Position
We Extending portion
1 Carrying support
2 Support main body
4A Grasping part main body
4B Press member 11 First grasping part
12 Second grasping part
13 Upper holding part
14 End portion holding member
15 Identification information part
16 Attachment part
20, 20A, and 20B Lateral frame
21 Vertical frame
22 and 23 Bracket
24 and 25 Projection
26 Knob portion
28 Attachment hole
30 Grasping portion
31 Hole part
32 Communication groove
33 Projection
34 and 35 Attachment hole
35b Guide groove
40 Grasping portion
41 Concave groove
43 Soft member
44 Hard member
45 Hard member
46 Soft member
50 Support rod
51 Holding part
52 and 53 Plate member
54 Bracket material
60 Attachment base
61 Projection
62 Posture change means
63 Processing part
64 Position adjustment means
65 Holding portion
66 Crease application processing part
67 Fold application processing part
68 Air supply/absorption means
69 Control valve
70 Leak tester
71 Display device
90 End member

DESCRIPTION OF EMBODIMENTS

Next, embodiments of the present invention will be described in detail with reference to the attached drawings.

A carrying support 1 of the present invention is a carrying support for use in the course of manufacturing medical tubes. As illustrated in FIGS. 1 and 2, the carrying support 1 is characterized by including a first grasping part 11 and a second grasping part 12 that grasp both end sides of work tubes W bent in the middle parts at upper position and extending downward (that is, the side of the work tubes W from the bent parts toward one end and the side of the work tubes W from the bent parts toward the other end). In the embodiment described below, the medical tube is a balloon catheter as illustrated in FIG. 7 as an example. However, the present invention is not limited to this but is applicable to various medical tubes such as other catheters and endoscopic treatment tools.

Specifically, the carrying support 1 includes a support main body 2 that is composed of a long lateral frame 20 and a vertical frame 21 erected upward from an approximately central position on the lateral frame 20. The horizontally-long first grasping part 11 is provided along one side (the left side of FIG. 1) of the lateral frame 20 with respect to the approximately central position on the lateral frame 20 where the vertical frame 21 is erected, and the second grasping part 12 is provided along the other side (the right side of FIG. 1) of the lateral frame 20 with respect to the approximately central position on the lateral frame 20. An upper holding part 13 is provided on the vertical frame 21 to hold the middle parts of the bent work tubes W at an upper position. There is no particular limitation on the material for the frame but the frame can be made of a metal such as aluminum or a hard synthetic resin.

The first grasping part 11 is attached to the front surface side of the lateral frame 20 in parallel to the frame, and the second grasping part 12 is attached to the back surface side of the lateral frame 20 in parallel to the frame. By providing the first grasping part 11 and the second grasping part 12 to the front and back opposite surfaces of the lateral frame 20 as described above, the weight of the work tubes W acts on the center of the lateral frame so that the long work tubes W can be held stably. As a matter of course, the first grasping part 11 and the second grasping part 12 may be provided to the same front or back surface of the lateral frame 20. In addition, provided on the same lateral frame 20, the first grasping part 11 and the second grasping part 12 are at almost the same height. Alternatively, they may be provided at different heights.

The first grasping part 11 and the second grasping part 12 each include a plurality of grasping portions 30 and 40 to grasp a plurality of (ten in the illustrated example) work tubes W at intervals as illustrated in FIGS. 3 to 5 so that the plurality of work tubes W can be collectively carried. However, there is no particular limitation on the number of the work tubes W grasped by the carrying support 1. As a matter of course, the present invention includes the configuration in which each of the grasping parts is capable of grasping one work tube (the grasping parts 11 and 12 each grasp only one work tube).

In addition, the first grasping part 11 and the second grasping part 12 each have a plurality of grasping portions 30 and 40 arranged in one line but the plurality of grasping portions 30 and 40 may be arranged in two or more lines. In the embodiment, as illustrated in the simplified planar view of FIG. 6(a), the linear first grasping part 11 and second grasping part 12 are provided along the linear lateral frame 20 so that the plurality of grasped work tubes W is supported on almost the same plane with excellent area productivity. However, the first grasping part 11 and the second grasping part 12 may be configured in a different manner.

For example, the first grasping part 11 and the second grasping part 12 may be provided in lateral frames 20A and 20B, respectively, opposed to each other in parallel as illustrated in FIG. 6(b). Alternatively, the lateral frame 20 may be bent at almost the central position and formed in a dogleg shape in a planar view so that the first grasping part 11 can be provided on the lateral frame 20 on one side with respect to almost the central position and the second grasping part 12 can be provided on the lateral frame 20 on the other side (the lateral frame 20 is bent at almost 90 degrees in the illustrated example but may be bent at a larger or smaller degree) as illustrated in FIG. 6(c). Still alternatively, the lateral frame 20 may be formed in an annular shape so that the first grasping part 11 and the second grasping part 12 can be provided at opposed positions as illustrated in FIG. 6(d). The first grasping part 11 and the second grasping part 12 are both configured to grasp the work tubes in the vertical direction but may be configured to grasp the work tubes obliquely.

The first grasping part 11 is an end portion grasping part that grasps end members 90 provided at first end portions w1 of the work tubes W in a positioned state, and the second grasping part 12 is an intermediate grasping part that grasps tube outer peripheral surfaces of the work tubes W from second end portions w3 to positions w2 nearer the center by a predetermined length. By setting one grasping part as an end portion grasping part to grasp the end portions w1 and setting the other grasping part as an intermediate grasping part as described above, it is possible to firmly fix the end portions w1 in a positioned state and support in a flexible state extending portions We of the predetermined length extending from the positions w2 grasped by the intermediate grasping part to the second end portions w3 as portions to be processed at the individual steps.

More specifically, as illustrated in FIG. 3, the first grasping part 11 includes a plurality of grasping portions 30 composed of hole portions 31 that are smaller in diameter than the end members 90 of the work tubes W (hub members in a balloon catheter) and penetrate vertically; and communication grooves 32 that have a width smaller than the diameter of the hole portions 31 and larger than the diameter of the tube portions of the work tubes W, extend laterally from the hole portions 31, and in this example, communicate with the outside through the front surface side opposite to the back surface side fixed to the lateral frame 20 of the support main body 2. In the state in which the relatively thin tube portions of the work tubes W are inserted into the hole portions 31 from the lateral side (front side) through the communication grooves 32, the work tubes W are further relatively moved along the long side in a direction in which the end members 90 approach the hole portions 31 (from the lower surface side to the upper surface side), whereby the end members 90 are press-fitted to the hole portions 31.

To maintain the stable press-fitted state of the end members 90, the entire first grasping part 11 or at least the hole portions 31 are preferably formed from a soft material such as a soft synthetic resin or a synthetic rubber. For example, polyoxymethylene (POM) or the like is preferred. In addition, since the groove structure is provided such that the grasping portions 30 are opened laterally by the hole portions 31 and the communication grooves 32 as described above, the first grasping part 11 is easy to be deformed by insertion of the end members 90 and can firmly grasp the end members 90 in the hole portions 31 by its elastic restoring force. In this example, for stably holding the end members 90 in the hole portions 31, projections 33 are formed on the inner peripheral surfaces of the hole portions 31 to enhance partly press-fitting force.

The first grasping part 11 is detachably attached to the lateral frame 20. Specifically, as illustrated in FIG. 4, the right and left end surfaces of the first grasping part 11 are detachably engaged between a pair of right and left attachment brackets 22 and 23 protruding from the front surface of the lateral frame 20. By detachably engaging the first grasping part 11 as described above, the plurality of work tubes W can be collectively set in an efficient manner such that, for example, while the first grasping part 11 is released from the lateral frame 20, the end members 90 of the work tube W are first grasped by the second grasping part 12 and then grasped by the first grasping part 11, and while all the work tubes W are grasped, the first grasping part 11 is attached to the lateral frame 20 while the work tubes W are bent.

More specifically, retractable projections 24 and 25 are provided on the opposed inner surfaces of the right and left brackets, at least one of which is spring-biased in a projecting direction, and the first grasping part 11 has attachment holes 34 and 35 on the corresponding right and left end surfaces into which the projections 24 and 25 are to be fitted. The retractable projection 25 is biased in the projecting direction by a spring not illustrated but built in the bracket 23, and the corresponding attachment hole 35 has a communicating guide groove 35b that is opened to the back side and has a tapered bottom surface becoming gradually shallower with increasing proximity to the front side.

To attach the first grasping part 11 to the lateral frame 20, while the projection 24 is inserted into the one attachment hole 34, the end portion of the first grasping part 11 on the other attachment hole 35 side is pressed against the front surface of the lateral frame 20. Accordingly, the guide groove 35b gradually presses and moves the projection 25 in a retracting direction, and the projection 25 projects again at the position of the attachment hole 35 and fits in the attachment hole 35. To remove the first grasping part 11, a knob portion 26 protruding from the bracket opposite surface of the projection 25 on the base end side is held and pulled by hand in the direction in which the projection 25 retracts to release the first grasping part 11 from the attachment hole 35. Accordingly, the first grasping part 11 can be removed with a one-touch action from between the brackets 22 and 23.

As illustrated in FIG. 5, the second grasping part 12 is fixed to the lateral frame 20 and is composed of a grasping part main body 4A in which a plurality of concave grooves 41 are formed at intervals on the outer surface and communicated with the upper and lower surfaces, and a plate-like press member 4B that is fixed by attachment screws 42 to the outer surface of the grasping part main body 4A to sandwich the tube outer peripheral surfaces of the work tubes W arranged in the concave grooves 41 between the press member 4B and the concave grooves 41. That is, the plurality of concave grooves 41 serves as a grasping portion 40 together with the press member 4B.

At least the concave grooves 41 and the inner surface side of the press member 4B opposed to the concave grooves 41 are preferably formed from a soft material such as a soft synthetic resin or a synthetic rubber to stably hold the tube outer peripheral surfaces without breakage. In this example, the grasping part main body 4A is structured to sandwich a soft member 43 (for example, silicone rubber) having the concave grooves 41 by a relatively hard member 44 (for example, polyoxymethylene (POM)), and the press member 4B has a two-layer structure of a relatively hard member 45 (for example, polyoxymethylene (POM)) and an inner soft member 46 (for example, silicone sponge) opposed to the concave grooves 41.

The upper holding part 13 is an approximately L-shaped hook viewed from the side that is provided on the front surface of the vertical frame 21 to lock the middle parts of the bent work tubes W as illustrated in FIGS. 1 and 2. By locking the work tubes W with the upper holding part 13 as described above, it is possible to stably hold the work tubes W such that the tube middle parts are not shaken during transportation, and prevent concentration of stress on the tube base parts grasped by the first grasping part 11 and the second grasping part 12.

The upper holding part 13 is preferably height-adjustable depending on the length of the work tubes W. The hook in this example can be selectively attached by an attachment screw 27 into a plurality of screw holes not illustrated but provided in the vertical frame 21. In addition, in the illustrated example, the work tubes W are locked at the inversely U-shaped bent portions. However, in the case where the work tubes W are still longer, the work tubes W may be locked in the state that they are rolled once or more and bound.

In addition, the upper holding part 13 in this example is configured to support the work tubes W between the vertical frame 21 and the hook such that the middle parts of the work tubes W do not fall. Alternatively, the upper holding part 13 may be configured to lock the work tubes W to support the load of the work tubes W, or may be configured to firmly fix the work tubes W onto the vertical frame 21 to support the load of the work tubes W. When the upper holding part 13 is configured to support the load of the work tubes W as described above, it is possible to further decrease the force of the first and second grasping parts for supporting the work tubes W, thereby to lighten the burden on the tubes.

The support main body 2 is provided with attachment parts 16 for attachment to the manufacturing devices used in the manufacturing process as illustrated in FIG. 4 and the enlarged view of FIG. 8. In this example, attachment holes 28 are formed in a plurality of places on the bottom surface of the lateral frame 20, and the plurality of projections 61 projected from the corresponding positions on the upper surface of an attachment base 60 on the manufacturing device side are fitted into the attachment holes 28 to attach the carrying support 1 grasping the work tubes W in a stable posture on the attachment base 60. The attachment parts 16 are not limited to these holes but may be projections fitted into holes in the attachment base 60 or may be configured in another mode, for example, engagement parts for mutual engagement to improve stability.

A plurality of manufacturing devices used in the manufacturing process each includes the attachment base 60 with the plurality of projections 61 in the same manner so that the attachment parts 16 can be used in common among the manufacturing devices. That is, the carrying support 1 according to the present invention can be attached to the manufacturing devices and serve as a jig for positioning the work tubes W to be processed.

In addition, the carrying support 1 of the embodiment has an end portion holding member 14 detachably attached to hold at a predetermined position the end portions w3 of the work tubes grasped at the tube outer peripheral surfaces by the second grasping part 12 and extending from the second grasping part 12. The end portion holding member 14 is specifically composed of two support rods 50 and 50 extending downward from the lateral frame 20 in the positions at the right and left both ends of the second grasping part 12 and a holding part 51 hung across the leading ends of the support rods as illustrated in FIGS. 1 and 2. The plurality of extending portions We of the work tubes is arranged in parallel inside the frame formed by the end portion holding member 14 and the second grasping part 12. In this example, bracket members 54 are provided at the upper ends of the support rods 50 so that the bracket members 54 can be detachably attached by attachment screws 55 to the lower surface of the lateral frame 20. Alternatively, any other mechanism may be employed to attach the end portion holding member 14 in a detachable manner.

The holding part 51 is configured to sandwich the tube end portions w3 between front and back plate members 52 and 53 such that the extending portions We inside the frame are laid between the second grasping part 12 and the holding part 51 as illustrated in FIG. 2. Accordingly, it is possible to carry the work tubes in a stable posture while the extending portions We to be processed are protected inside the frame and are not in contact with one another. The work tubes can be processed with the end portion holding member 14 remaining attached at the step of coating such as dipping and subsequent drying step and others.

An identification information part 15 from which information is read by a reading device as necessary in the manufacturing process is added to the support main body 2 or another appropriate part. The identification information part 15 may be preferably a bar code or an ID tag into which information can be written. Accordingly, the information on the attached work tubes W such as serial numbers can be obtained to facilitate precise processing and management without error according to the product type.

Next, an embodiment of a manufacturing device in which the carrying support 1 according to the present invention is also used as a jig will be explained with reference to FIGS. 8 to 13.

A manufacturing device A2 of the embodiment includes, as illustrated in FIGS. 8 and 9, an attachment base 60 to which the carrying support 1 grasping a plurality of work tubes W is attached, a posture change means 62 for changing a plurality of extending portions We of the work tubes W supported by the carrying support 1 attached to the attachment base 60 and extending from a second grasping part 12 to end portions w3 into a predetermined posture while selectively bending the extending portions We, and a processing part 63 that processes the extending portions We sequentially changed into different postures by the posture change means 62.

A plurality of projections 61 is provided on the upper surface of the attachment base 60 at positions corresponding to a plurality of attachment holes 28 as attachment parts 16 of the carrying support 1. Accordingly, the work tubes W are positioned and set on the attachment base 60 through the carrying support 1. That is, the carrying support 1 serves as a jig for processing the work tubes W at the manufacturing device A2.

The posture change means 62 is an extraction mechanism by which the plurality of extending portions We in a line among which clearances are too small to process is selectively extracted from the line for processing. The posture change means 62 is composed of a plurality of holding portions 65 holding the extending portions We and a movement mechanism not illustrated that moves the holding portions 65 to predetermined positions to change the held extending portions We into a predetermined posture. The movement mechanism may be any one of various mechanisms by which to move the holding portions 65 along slide rails or move the holding portions 65 via a hydraulic cylinder, a link, or the like.

In this example, the manufacturing device A2 is configured as a fold processing apparatus for balloon catheters. The processing part 63 is a balloon fold processing part but may not be limited to this. The processing part 63 can be any one of a wide range of publicly known processing parts that individually process the extending portions We of the work tubes W as medical tubes. In this example, the processing part 63 specifically includes as the fold processing part a crease application processing part 66 that forms creases in balloons and a fold application processing part 67 that folds the creases formed by the crease application process in a circumferential direction to form folds.

In addition, in the embodiment, a position adjustment means 64 is provided to sequentially adjust the relative positions of the extending portions We sequentially changed in posture by the posture change means 62 and the processing part 63 such that the relative positional relationship becomes constant. The position adjustment means 64 is not illustrated in the drawing but can be any one of publicly known feeding mechanisms that laterally moves the attachment base 60 or the processing part 63.

Further, in the embodiment, an air supply/absorption means 68 is provided and connected to hubs having a port for supply of a pressure fluid as end members 90 on the base end side. The air supply/absorption means 68 is connected to a control valve or the like not illustrated by which to select hubs to/from which the air is supplied/absorbed, for example, and supplies or absorbs the air as necessary when the extending portions We are processed by the processing part 63 or the like.

In addition, although not illustrated, a control device composed of a computer is provided to automatically control the operations of the posture change means 62, the processing part 63, the position adjustment means 64, the air supply/absorption means 68, and others. The manufacturing device A2 operates as described below.

First, the posture change means 62 once turns all the extending portions We from the vertically downward position into an avoidance posture in which they are bent toward the left side of the drawing as illustrated in FIG. 10(a), and then the posture change means 62 changes one of the extending portions We in posture such that it is axially positioned on the crease application processing part 66 (the vertically downward position in this example) as illustrated in FIG. 10(b).

Then, the crease application processing part 66 axially moves toward the extending portion We changed in posture and processes the extending portion We as illustrated in FIG. 11(a), and then the crease application processing part 66 returns to the original position as illustrated in FIG. 11(b).

Next, the posture change means 62 further changes the extending portion We processed by the crease application processing part 66 into a posture in which it bends rightward up to an axial position on the fold application processing part 67 as illustrated in FIG. 12(a), and the fold application processing part 67 axially moves toward the extending portion We and processes the extending portion We as illustrated in FIG. 12(b), and then returns to the original position as illustrated in FIG. 13(a).

The processed extending portion We returns to the avoidance position to which the other extending portions We were moved leftward by the posture change means 62. Then, the carrying support 1 and the entire work tubes W move together with the attachment base 60 such that the position adjustment means 64 can place the adjacent unprocessed extending portion We into the position corresponding to the processing part 63. Subsequently, the same operation is performed to process the adjacent extending portions We in sequence in the same manner.

In the foregoing example, the first extending portion We is processed by the crease application processing part 66 and the fold application processing part 67, and then the next (second) extending portion We is processed by the crease application processing part 66 and the fold application processing part 67 in the same manner as the first extending portion We. However, the present invention is not limited to this mode. For example, as illustrated in FIGS. 16(a) and 16(b), the fold application processing part 67 is not only separated from the crease application processing part 66 in a depth direction (in a direction from the front side to back side of the plane in FIG. 16(a)) but also arranged at a position shifted by the same distance as an arrangement interval (pitch) in the direction in which the extending portions We are arranged (in the direction of feeding by the position adjustment means 64) so that the extending portions We can be processed by such operations as described below.

That is, for example, the first extending portion We is processed by the crease application processing part 66 as illustrated in FIGS. 11(a) and 11(b) in the same manner as described above, and then is changed in posture up to the position of the fold application processing part 67 shifted by the foregoing pitch for fold application process. At the same timing as the posture change, the next second extending portion We in the avoidance position is also changed in posture up to the position of the crease application processing part 66 shifted by the pitch for crease application process as illustrated in FIG. 16(a). Next, the position adjustment means 64 moves the entire work tubes W by one pitch as illustrated in FIG. 16(b) so that the first extending portion We and the second extending portion We can be coaxial with the fold application processing part 67 and the crease application processing part 66, respectively.

Then, as illustrated in FIG. 17(a), the fold application processing part 67 and the crease application processing part 66 are moved at the same time toward the first extending portion We and the second extending portion We for processing. Next, as illustrated in FIG. 17(b), the first extending portion We after the fold application process is changed in posture up to the avoidance position, and the second extending portion after the crease application process is changed in posture up to the position of the fold application processing part 67 shifted by the foregoing pitch for fold application process. At the same timing as the posture change of the two extending portions, the next third extending portion We in the avoidance position is also changed in posture up to the position of the crease application processing part 66 shifted by the foregoing pitch for crease application process.

Subsequently, the position adjustment means 64 further moves the entire work tubes W by one pitch, the second extending portion We and the third extending portion We are processed at the same time, and the next one extending portion is changed in posture at the same time as the posture change of the processed two extending portions, and two each extending portions are sequentially processed at the same time, in the same manner as described above. Accordingly, the crease application processing and the fold application processing can be performed at the almost same time, thereby achieving favorable production efficiency. In this example, the position adjustment means 64 moves the extending portions at the timing immediately before the processing of the extending portions We changed in posture. As a matter of course, alternatively, the extending portions We can be moved at the timing immediately before the posture change immediately after the processing. In addition, the work tubes W are moved in this example, but as a matter of course, the processing parts (the crease application processing part 66 and the fold application processing part 67) may be moved while the positional relationship is kept constant.

As an alternative example, the crease application processing part 66 sequentially processes all the extending portions We, and then the fold application processing part 67 sequentially processes all the extending portions We after the crease application process.

Next, a manufacturing system for manufacturing medical tubes by performing processes at a plurality of manufacturing devices A1 to A3 with the use of the carrying support 1 of the present invention will be described.

In the manufacturing system, as illustrated in FIGS. 14 and 15, the plurality of manufacturing devices A1 to A3 are arranged in a plant according to the process sequence. The manufacturing devices A1 and A2 are processing devices that are each provided with an attachment base 60 for attachment of the carrying support 1 grasping work tubes W and a processing part 63 that is supported by the carrying support 1 attached to the attachment base 60 to process a plurality of extending portions We extended from the second grasping part 12 to end portions w3. The work tubes W grasped by the carrying support 1 are carried to the manufacturing devices A1 and A2. Then, the work tubes W grasped by the carrying support 1 are processed at the manufacturing devices. The manufacturing device A3 is a withstand pressure test device.

The manufacturing device A1 is a dip coating device that applies surface coating to predetermined areas of the extending portions We. As illustrated in FIGS. 14(b) and 14(b'), the manufacturing device A1 is provided with an air supply/absorption means 68 connected to hubs as end members 90 on the base end side and a coating bath as the processing part 63. The attachment base 60 is provided with a movement mechanism that moves upward and downward the entire carrying support 1 grasping the work tubes W and is configured to immerse the extending portions We in the coating bath up to a predetermined depth.

The carrying support 1 carried to the manufacturing device A1 is provided in advance with the end portion holding member 14 as described above holding the end portions w3 of the work tubes. At the manufacturing device A, the extending portions We are immersed together with the end portion holding member 14 in the coating bath, and are carried together with the end portion holding member 14 while being dried at the next carrying step. Similarly, the balloons are kept in the bulging state by the air supply/absorption means 68 during coating and drying at the manufacturing device A1.

The manufacturing device A2 is as described above and further explanations thereof will be omitted. FIG. 15(b) illustrates an example in which a withstand pressure test device is provided as the manufacturing device A3. In this example, the withstand pressure test device is connected to a leak tester 70 that supplies the air to the hubs on the base end side through a control valve 69 to test the amount of leakage. The withstand pressure test device has a means that reads information from the identification information part 15 of the carrying support 1, adds information on the result of the withstand pressure test to the read information, and stores the same in a server computer or the identification information part 15.

FIG. 15(d) illustrates a step where an appearance test is performed and the work tubes W are removed from the carrying support 1. At this step, a display device 71 is provided to read information from the identification information part 15 and outputs the information on the result of the withstand pressure test, and the work tubes determined as defective at the withstand pressure test or the appearance test are put into a defective product container.

The work tubes W may be carried between the manufacturing devices A1 to A3 and the appearance test step by the operator manually holding the carrying support 1 grasping the work tubes W or by a publicly-known delivery mechanism such as a conveyor capable of transferring the carrying support 1.

Embodiment of the manufacturing system with the use of the carrying support 1 has been described so far. However, the manufacturing system of the present invention is not limited to the foregoing devices and process sequence. As a matter of course, the present invention is also applicable to processing devices, test devices, steps, and others according to the type of the medical tubes.

Embodiments of the present invention have been described so far. However, as a matter of course, the present invention is not limited to the foregoing examples but can be carried out in various modes without deviating from the gist of the present invention.

The invention claimed is:

1. A carrying support for holding work tubes having end portions in the manufacturing process of medical tubes, comprising:
   a first holding part for holding the work tubes;
   a second holding part for holding the work tubes, and
   an upper holding part, wherein
   the first holding part and the second holding part are arranged so that the work tubes are bent such that middle portions of the work tubes extend upwardly and the first and the second ends of the work tubes extend downwardly, and
   the upper holding part is disposed at a higher position than the first and second holding parts such that the upper holding part holds the middle portions of the bent work tubes.

2. The carrying support according to claim 1, wherein the first holding part and the second holding part each have a plurality of grasping portions for each grasping the plurality of work tubes at intervals, so that the plurality of work tubes can be carried at once.

3. The carrying support according to claim 2, wherein the plurality of grasping portions of the first holding part is arranged in an approximately linear fashion at intervals,
   the plurality of grasping portions of the second holding part is arranged in an approximately linear fashion at intervals, and
   the first holding part and the second holding part are provided on substantially the same plane.

4. The carrying support according to claim 1, wherein the upper holding part is height-adjustable.

5. The carrying support according to claim 1, wherein at least one of the first holding part and the second holding part is arranged to hold outer peripheral surfaces of the work tubes at positions away from the end portions of the work tubes by a predetermined length.

6. The carrying support according to claim 1, wherein the first and second holding parts are arranged so that the first holding part holds end members provided at first ends of the work tubes, and the second holding part holds outer peripheral surfaces of the work tubes at positions distant by a predetermined length from second ends of the work tubes.

7. The carrying support according to claim 5, further comprising an end portion holding member, wherein
   the first and second holding parts and the end portion holding member are arranged so that i) the outer peripheral surfaces of the work tubes are held by one of the first and second holding parts, ii) the other of the first and second holding parts holds the outer peripheral surfaces of the work tubes such that the work tubes downwardly extends by the predetermined length from the other of the first and second holding parts, and iii) the end portion holding member is detachably provided to hold the end portions of the work tubes which downwardly extend from the other of the first and second holding parts.

8. The carrying support according to claim 1, further comprising an identification information part capable of being read by a reading device.

9. The carrying support according to claim 1, further comprising an attachment part for attaching the carrying support to a manufacturing device for manufacturing medical tubes.

10. A medical tube manufacturing system for manufacturing medical tubes by performing processes at a plurality of manufacturing devices with the carrying support according to claim 1, the system comprising:
the carrying support for holding a plurality of work tubes such that the work tubes are held by one of the first and second holding parts at outer peripheral surfaces of the work tubes at positions away from the end portions of the work tubes by the predetermined length and the work tubes downwardly extends from said one of the first and second holding parts; and
the plurality of manufacturing devices, wherein
the plurality of manufacturing devices is arranged,
each of the manufacturing devices comprises:
an attachment base to which the carrying support is attached; and
a processing part that processes portions of the work tubes which downwardly extends from said one of the first and second holding parts, wherein
the carrying support is arranged such that the work tubes held by the carrying support are carried to the manufacturing devices, and the work tubes held by the carrying support are processed by the manufacturing devices.

11. A medical tube manufacturing device using the carrying support according to claim 1, comprising:
the carrying support for holding the plurality of work tubes by the first holding part and the second holding part such that the work tubes downwardly extends from one of the first and second holding parts;
an attachment base to which the carrying support holding the plurality of work tubes by the first holding part and the second holding part is attached;
a posture change means that, in the plurality of work tubes supported by the carrying support attached to the attachment base and held at the outer peripheral surfaces of the work tubes at positions away from the end portions of the work tubes by the predetermined length by the first holding part or the second holding part, changes the plurality of extending portions extending from said one of the first and second holding parts to the end portions into a predetermined posture while selectively bending the extending portions; and
a processing part that processes the extending portions sequentially changed into different postures by the posture change means.

12. The medical tube manufacturing device according to claim 11, comprising a position adjustment means that sequentially adjusts relative positions of the extending portions sequentially changed in posture by the posture change means and the processing part such that the relative positional relationship becomes constant.

13. The medical tube manufacturing device according to claim 11, further comprising an air supply/absorption means, wherein
the medical tubes are balloon catheters,
the extending portions are leading end-side portions having balloons, and
the air supply/absorption means is connected to hubs to be connected to other end of the balloon catheters.

14. The medical tube manufacturing device according to claim 13, wherein the processing part is a fold processing part for the balloons and is configured as a balloon fold processing device for the balloon catheters.

15. The medical tube manufacturing device according to claim 14, wherein the processing part includes, as the fold processing part, a crease application processing part that forms creases in the balloons and a fold application processing part that folds the creases formed by the crease application process in a circumferential direction to form folds.

16. A medical tube manufacturing method for manufacturing medical tubes by performing processes at a plurality of manufacturing devices with the carrying support according to claim 1, wherein
the plurality of manufacturing devices is arranged,
each of the manufacturing devices includes an attachment base to which the carrying support holding the work tubes by the first holding part and the second holding part is attached and a processing part that processes extending portions of the work tubes held at the tube outer peripheral surfaces at positions away from the end portions of the work tubes by the predetermined length by the first holding part or the second holding part of the carrying support attached to the attachment base and extending from the holding part to the end portions,
the work tubes held by the carrying support are carried to the manufacturing devices,
the carrying support is attached to the attachment bases of the manufacturing devices, and
the work tubes held by the carrying support are processed by the processing parts of the manufacturing devices.

17. A medical tube manufacturing method with the carrying support according to claim 1, wherein
the carrying support holding the plurality of work tubes by the first holding part and the second holding part is attached to an attachment base,
in the plurality of work tubes supported by the carrying support attached to the attachment base and held at the tube outer peripheral surfaces at positions away from the end portions of the work tubes by predetermined length by the first holding part or the second holding part, a plurality of extending portions extending from the holding part to the end portions is changed into a predetermined posture while selectively bending the extending portions, and
the extending portions sequentially changed into different postures are processed.

18. The medical tube manufacturing method according to claim 17, wherein relative positions of the extending portions sequentially changed in posture and the processing part performing the process are sequentially adjusted such that the relative positional relationship becomes constant.

19. The medical tube manufacturing method according to claim 17, wherein
the medical tubes are balloon catheters,
the extending portions are leading end-side portions having balloons, and
the leading end-side portions having the balloons are processed while air is supplied or absorbed by an air supply/absorption means connected to hubs to be connected to other end of the balloon catheters.

20. The medical tube manufacturing method according to claim 19, wherein the process is a fold process for the balloons.

21. The medical tube manufacturing method according to claim 20, wherein the process includes, as the fold process, a crease application process for forming creases in the balloons and a fold application process for folding the creases formed by the crease application process in a circumferential direction to form folds.

* * * * *